United States Patent
Dewey et al.

(10) Patent No.: US 11,214,813 B2
(45) Date of Patent: *Jan. 4, 2022

(54) TARGETED MUTAGENESIS OF TOBACCO BERBERINE BRIDGE ENZYME-LIKE NUCLEIC ACIDS

(71) Applicant: North Carolina State University, Raleigh, NC (US)

(72) Inventors: Ralph E. Dewey, Apex, NC (US); Ramsey S. Lewis, Apex, NC (US)

(73) Assignee: NORTH CAROLINA STATE UNIVERSITY, Raleigh, NC (US)

(*) Notice: Subject to any disclaimer, the term of this patent is extended or adjusted under 35 U.S.C. 154(b) by 65 days.

This patent is subject to a terminal disclaimer.

(21) Appl. No.: 16/778,780

(22) Filed: Jan. 31, 2020

(65) Prior Publication Data

US 2020/0231980 A1 Jul. 23, 2020

Related U.S. Application Data

(63) Continuation of application No. 15/780,354, filed as application No. PCT/US2016/064758 on Dec. 2, 2016, now Pat. No. 10,590,429.

(60) Provisional application No. 62/263,151, filed on Dec. 4, 2015.

(51) Int. Cl.
| | |
|---|---|
| *C12N 15/82* | (2006.01) |
| *A01H 6/82* | (2018.01) |
| *C12N 15/52* | (2006.01) |
| *A01H 5/12* | (2018.01) |
| *A24D 1/00* | (2020.01) |

(52) U.S. Cl.
CPC .......... *C12N 15/8243* (2013.01); *A01H 5/12* (2013.01); *C12N 15/52* (2013.01); *C12N 15/8213* (2013.01); *A24D 1/00* (2013.01)

(58) Field of Classification Search
None
See application file for complete search history.

(56) References Cited

U.S. PATENT DOCUMENTS 10,590,429 B2 * 3/2020 Dewey ............... C12N 15/52
2009/0119806 A1 5/2009 Mallmann et al.

FOREIGN PATENT DOCUMENTS

| RU | 2403831 | 11/2010 |
| WO | 2006/109197 | 10/2006 |

OTHER PUBLICATIONS

Kajikawa et al, 2011, Plant Physiology, 155:2010-2022.*
Dewey et al, 2013, Phytochemistry, 94:10-27.*
Lopez, 2011, "Developing Non-GMO Tobacco Cultivars with Lower Alkaloid Content Using a Reverse Genetics Strategy", Thesis for Masters of Science, North Carolina State University Raleigh, North Carolina.*
Dewey et al. "Molecular genetics of alkaloid biosynthesis in *Nicotiana tabacum*" Phytochemistry, 94:10-27 (2013).
Extended European Search Report corresponding to European Patent Application No. 16871634.8, dated Mar. 20, 2019, 9 pages.
GenBank Database Database accession No. AB604221.1, (2011).
Kajikawa et al. "Vacuole-Localized Berberine Bridge Enzyme-Like Proteins are Required for a Late Step of Nicotine Biosynthesis in Tobacco" Plant Physiology, 155(4):2010-2022 (2011).
Lewis et al., "Transgenic and Mutation-Based Suppression of a Berberine Bridge Enzyme-Like (BBL) Gene Family Reduces Alkaloid Content in Field-Grown Tobacco", PLoS One, 10:2, 17 pages (2015).
Written Opinion of International Search Report corresponding to International Application No. PCT/US2016/064758, dated Mar. 16, 2017, 5 pages.
Lopez "Developing Non-GMO Tobacco Cultivars with Lower Alkaloid Content Using a Revers Genetics Strategy" Thesis for Masters of Science, North Carolina State University, 2011, 120 pages.
Goossens et al. "A functional genomics approach toward the understanding of secondary metabolism in plant cells", PNAS, 100(14):8595-8600 2003.
GenBank Database accession No. XM_009785405.1, 2014, accessed on Jul. 21, 2020 at https://www.ncbi.nlm.nih.gov/nuccore/XM_009785405.1.

* cited by examiner

Primary Examiner — Jason Deveau Rosen
(74) Attorney, Agent, or Firm — Myers Bigel, P.A.

(57) ABSTRACT

The present invention relates to modifications of berberine bridge enzyme-like nucleic acids and their use in modulation of nicotine biosynthesis in plants.

12 Claims, 1 Drawing Sheet

Specification includes a Sequence Listing.

Fig. 1A

```
BBLe    CATCTTACATGCCGAAACCAACGGTCATTATCCTACCAAACAGCAAACAGGAGCTTCTAAGTACCATTCTTTGTTGCAGACAA  (Wild Type) (SEQ ID NO:9)
#7      CATCTTACATGCCGAAACCAACGGTCATTATCCTACCAAACAGCAAACAGGAGCAGAG------GGTACCATTCTTTGTTGCAGACAA  (-6) (SEQ ID NO:10)
#21     CATCTTACATGCCGAAACCAACGGTCATTATCCTACCAAACAGCAAACAGCAAACAGAG--ACTACCATTCTTTGTTGCAGACAA  (-2) (SEQ ID NO:11)
#53     CATCTTACATGCCGAAACCAACGGTCATTATCCTACCAAACAGCAAACAGCAAACAGAG--AGTACCATTCTTTGTTGCAGACAA  (-9) (SEQ ID NO:12)
#85     CATCT-------ATTAACCCACAAGAATGATCAAGTA--------------------------AGTACCATTCTTTGTTGCAGACAA  (-54, +28) (SEQ ID NO:13)
#115    CATCTTACATGCCGAAACCAACGGTCATTATCCTACCAAACAGCAAACAGCAAACAGAAGAAAGCT---TCTTACACTTG--  (-19, +11) (SEQ ID NO:14)
#143*   CATCTTACATGCCGAAACCAACGGTCATTATCCTACCAAACAGCAAACAGCAAACAGAGA---------------TGCAGACAA  (-14) (SEQ ID NO:15)
#206    CATCTTACATGCCGAAACCAACGGTCATTATCCTACCAAACAGCAAACAGCAAACAGAGCTTG--TTCTTTGTTGCAGACAA  (-1) (SEQ ID NO:16)
#209    CATCTTACATGCCGAAACCAACGGTCATTATCC--------------------------------AGTACCATTCTTTGTTGCAGACAA  (-31) (SEQ ID NO:17)
```

Fig. 1B

```
BBL-d1  TCTCCGATTCGCAGCGTGCTCTAAACCAAACCAACTGTCATTATCGTACCAGAGCAGCAAGGAGCAGCTGGT  (Wild Type) (SEQ ID NO:18)
#36     --------AACTAGTCTAA-----------------------------ACCAGCAGCAAGGAGCAGCTGGT  (-106, +11) (SEQ ID NO:19)
#42     TCTCCGATTCGCAGCGTGCTCTAAACCAAAC--------------TACCAGCAGCAAGGAGCAGCTGGT  (-15) (SEQ ID NO:20)
#71     TCTCCGATTCGCAGCGTGCTCTAAACCAAACCAACTGTCATTATCGTAC-AGCAGCAAGGAGCAGCTGGT  (-1) (SEQ ID NO:21)
#100    TCTCCGATTCGCAGCGTGCTCTAAACCAAACCAACTGTC---------AGGAGCAGGTGGT  (-18) (SEQ ID NO:22)
#128    TCTCCGATTCGCAGCGTGCTCTAAACCAAACCAACTGTCATTATCGTAATAGTAACTATCATTAACCAGAGCAGAAGGAGCAGCTGGT  (+12) (SEQ ID NO:23)
#135    TCTCCGATTCGCAGCGT------------------------A------TACCAGCAGCAGCAAGGAGCAGCTGGT  (-29) (SEQ ID NO:24)
#139    TCTCCGATTCGCAGCGT-------------------------------AGGT  (-19) (SEQ ID NO:25)
#201    TCTCCGATTCGCAGCGTGCTCTAAACCAAACCAACTGTC--GCA-GTACAGAGCAGAGCACAGGAG-AGGAGCAGCTGGT  (-6, +3) (SEQ ID NO:26)
```

Fig. 1C

```
BBL-d2  TCTCCGATTCGCAGCGTCCTCCTAAACCAAACCAAACCAACGGTCATTATCGTACCAGAGCAGCAAGGAGCAGCTGGT  (Wild Type) (SEQ ID NO:27)
#29     TCTCCGATTCGCAGCGTCCTCCTAAACCAAACCAAACCAACGGTCATTA-------CCAGAGCAGCAAGGAGCAGCTGGT  (-5) (SEQ ID NO:28)
#31     TCTCCGATTCGCAGCGTCCTCCTAA-------------------TGAAATCAGAGTA------AGCTGGT  (-41, +13) (SEQ ID NO:29)
#36*    TCTCCGATTCGCAGCGTCCTCCTAAACCAAACCAAACCAACGGTCATTATCTTACACAGTGTTATGAAGCAGAG  (-2, +19) (SEQ ID NO:30)
#44     TCTCCGATTCGCAGCGTCCTCCTAAACCAAACCAAACCAA-------------------GGAGCAGCAGCAGT  (-25) (SEQ ID NO:31)
#100    TCTCCGATTCGCAGCGTCCTCCTAAACCAAACCAAACCAACGGTCATTATC-----AGGAGCAGCAGCAGT  (-5) (SEQ ID NO:32)
#101    TCTCCGATTCGCAGCGTCCTCCTAAACCAAACCAAACCAACG-------TTAAAA-----AGGAGCAGCAGT  (-21, +6) (SEQ ID NO:33)
#104    TCTCCGATTCGCAGCGTCCTCCTAAACCAAACCAAACCAACG-----------------AACAGCTGGT  (-25) (SEQ ID NO:34)
#138    TCTCCGATTCGCAGCGTCCTCCTAAACCAAACCAAACCAAC-------------------AACAGCCGCTGGT  (-39) (SEQ ID NO:35)
#201    TCTCCGATTCGCAGCG-----------------------CAGAGCAGAGGAGCAGCTGGT  (-14) (SEQ ID NO:36)
#205    TCTCCGATTCGCAGCGTCCTCCTAAACCAAACCAAACCAAAACCAAC-----------------GCTGGT  (-16) (SEQ ID NO:37)
```

TARGETED MUTAGENESIS OF TOBACCO BERBERINE BRIDGE ENZYME-LIKE NUCLEIC ACIDS

STATEMENT OF PRIORITY

This application is a continuation application of U.S. application Ser. No. 15/780,354, filed on May 31, 2018, which is a 35 U.S.C. § 371 national phase application of International Application Ser. No. PCT/US2016/064758, filed Dec. 2, 2016, which claims the benefit, under 35 U.S.C. § 119 (a) of U.S. Provisional Patent Application No. 62/263,151, filed Dec. 4, 2015, the entire contents of each of which are incorporated by reference herein.

FIELD OF THE INVENTION

The present invention relates to modifications of berberine bridge enzyme-like nucleic acids and their use in modulation of nicotinic alkaloid biosynthesis in plants.

BACKGROUND OF THE INVENTION

The pyridine alkaloids of tobacco (*Nicotiana tabacum* L.) are among the most studied group of plant secondary compounds. Nicotine constitutes greater than 90% of the total alkaloid pool in most tobacco genotypes and is primarily responsible for the pharmacological response experienced by users of tobacco products. In decreasing order of relative abundance, the remaining major alkaloids in tobacco include anatabine, nornicotine, and anabasine. Alkaloid levels in tobacco are influenced by environmental conditions, interactions with plant pests, and plant genetics.

Although nicotine is the primary compound that gives the users of tobacco products the pharmacological effect they seek, there are several circumstances where it would be desirable to develop products using tobacco plants that produce and accumulate very low levels of nicotine. For example, some studies have shown that the use of low-nicotine cigarettes as a component in smoking cessation strategies can help smokers who are trying to quit (Hatsukami et al., 2010a; Donny et al., 2014). Other reports have demonstrated that by lowering the nicotine levels below a critical threshold in tobacco products, they can no longer initiate or maintain an addiction response (Benowitz and Henningfield, 1994; Benowitz et al., 2007). Studies such as these may ultimately influence regulatory agencies, such as the U.S. Food and Drug Administration, who have been given the authority to determine what acceptable levels of various tobacco constituents (including nicotine) will be allowable in cigarettes and other tobacco products.

Tobacco alkaloid levels are also of interest because of their role in the production of tobacco specific nitrosamines (TSNAs), a potent group of recognized carcinogens (Hecht, 1998, 2003; Hecht and Hoffman, 1989). The most important TSNAs are N-nitrosonornicotine (NNN) and 4-(methylnitrosamino)-1-(3-pyridyl)-1-butanone (NNK), which are derived through nitrosation reactions with nornicotine and an oxidative derivative of nicotine (such as pseudooxynicotine), respectively, during the curing, storage, and consumption of tobacco. Because tobacco alkaloids serve as precursors toward TSNA formation, low alkaloid tobacco plants have also been shown to produce reduced amounts of TSNAs within the cured leaf (Xie et al., 2004). Further, while modifications in the curing environment have led to substantial TSNA reductions in flue-cured tobacco varieties, this has not been the case in the air-cured burley tobacco types.

This invention addresses the need for compositions and methods that modulate the nicotine biosynthesis pathway in plants.

SUMMARY OF THE INVENTION

In one aspect, the present invention provides a method of producing a *Nicotiana* plant having reduced nicotinic alkaloid content, comprising introducing into the plant (a) a mutation in an endogenous BBLe polynucleotide having 97% identity to the nucleotide sequence of SEQ ID NO:3, (b) a mutation in an endogenous BBLd-1 polynucleotide having 97% identity to the nucleotide sequence of SEQ ID NO:1, and/or (c) a mutation in an endogenous BBLd-2 polynucleotide having 97% identity to the nucleotide sequence of SEQ ID NO:2, thereby producing a plant having reduced nicotinic alkaloid content.

In a second aspect, a plant having reduced nicotinic alkaloid content is provided, the plant comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2.

The present invention further provides plants and plant parts thereof produced by the methods of the invention as well as crops and products produced from said plants and parts thereof. The present invention further provides vectors and expression cassettes for carrying out the methods of the invention.

These and other aspects of the invention are set forth in more detail in the description of the invention below.

BRIEF DESCRIPTION OF THE FIGURES

FIG. 1A-1C show genome editing events using custom-designed meganuclease constructs. Wild type sequences in the targeted region of BBLe (FIG. 1A), BBLd-1 (FIG. 1B) and BBLd-2 (FIG. 1C) are shown above the various mutation events that were identified at that locus. Nucleotides in bold and italics show an exemplary 22 bp target site of a designer nuclease. Dashes represent nucleotides that have been deleted, and nucleotides shaded grey represent small insertions. Numbers in parentheses at the right of each $T_0$ plant indicate the size of the deletion and/or insertion event(s) in that plant. In $T_0$ plants with an asterisk, the indicated mutation is predicted to be biallelic (i.e. homozygous). For all other $T_0$ plants the mutation is predicted to be monoallelic (heterozygous). $T_0$ events are underlined whose net loss or gain of nucleotides at the mutation site is not divisible by three (therefore ensuring that reading frame downstream of the mutation would not be contiguous with the wild type reading frame).

DETAILED DESCRIPTION OF THE INVENTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention.

For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "chimeric" refers to a nucleic acid molecule or a polypeptide in which at least two components are derived from different sources (e.g., different organisms, different coding regions).

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express, for example, a polypeptide of interest or a functional untranslated RNA.

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or substantially identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent.

As used herein, the term "gene" refers to a nucleic acid molecule capable of being used to produce mRNA, antisense RNA, RNAi (miRNA, siRNA, shRNA), anti-microRNA antisense oligodeoxyribonucleotide (AMO), and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "heterologous" or a "recombinant" nucleic acid is a nucleotide sequence not naturally associated with a host cell into which it is introduced, including non-naturally occurring multiple copies of a naturally occurring nucleotide sequence. Alternatively, a heterologous nucleotide sequence can be one that does not naturally occur with another nucleotide sequence to which it is associated. For example, a nucleic acid construct comprising a "heterologous promoter" operably associated with a nucleic acid molecule is a promoter that does not naturally occur with said nucleic acid molecule to which it is associated.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention. In some embodiments, an endogenous BBLe polynucleotide can have about 97% identity (e.g., about 97, 98, 99, or 100% identity) to the nucleotide sequence of SEQ ID NO:3, In some embodiments, an endogenous BBLd-1 polynucleotide can have about 97% identity (e.g., about 97, 98, 99, or 100% identity) to the nucleotide sequence of SEQ ID NO:1. In some embodiments, an endogenous BBLd-2 polynucleotide can have about 97% identity (e.g., about 97, 98, 99, or 100% identity) to the nucleotide sequence of SEQ ID NO:2.

As used herein, hybridization, hybridize, hybridizing, and grammatical variations thereof, refer to the binding of two fully complementary nucleotide sequences or substantially complementary sequences in which some mismatched base pairs may be present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 15%, 25%, 50%, 75%, 100%, 150%, 200%, 300%, 400%, 500% or more as compared to a control.

As used herein, "modify," "modifying" or "modification" (and grammatical variations thereof) of a means any alteration of a BBL polynucleotide (e.g., BBLe, BBLd-1, BBLd-2) and/or BBL polypeptide or other polypeptide or polynucleotide that results in the reduction or elimination of the expression of the nucleic acids and/or the production and/or activity of the polypeptides. Such modifications can include, but are not limited to, deleting or inserting one or more nucleotides or an entire nucleic acid region (transcribed and untranscribed regions), and/or introducing one or more point mutations, which reduce or eliminate the expression of the nucleic acids and/or the production and/or activity of the polypeptides.

As used herein, the terms "modulate," "modulates," "modulated" or "modulation" refer to enhancement (e.g., an increase) or inhibition (e.g., a reduction) in a specified activity (e.g., modulated nicotine production/content). Thus, in some embodiments, an elevation or increase in activity (e.g., nuclease activity) of about 15%, 25%, 50%, 75%, 100%, 150%, 200%, 300%, 400%, 500% or more as compared to a control may be observed. In other embodiments, a reduction in expression level or activity (e.g., BBLe, BBLd-1, BBLd-2 expression level or BBLe, BBLd-1, BBLd-2 polypeptide activity) of about 30%, 35%, 40%, 45%, 50%, 55%, 60%, 65%, 70%, 75%, 80%, 85%, 90%, 95%, 96%, 97%, 98%, 99%, or 100% as compared to a control.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is a mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

As used herein, "nicotinic alkaloid" refers to alkaloids derived from nicotinic acid. These alkaloids generally contain a 3-pyridyl ring structure, with nicotine, nornicotine, anatabine and anabasine representing the predominant nicotinic alkaloids within the genus *Nicotiana*. In some embodiments, a nicotinic alkaloid may comprise, consist essentially of, or consist of nicotine, nornicotine, anatabine and/or anabasine.

As used herein, "alkaloid content" means the total amount of alkaloids found in a plant, for example, in terms of percent dry weight (% dry weight) or percent fresh weight (% fresh weight).

A plant useful with this invention can be any *Nicotiana* plant that produces nicotine and/or other related alkaloids. Thus, in some embodiments, the plant can be *Nicotiana tabacum, Nicotiana rustica* or *Nicotiana benthamiana*. Any variety of tobacco is useful with this invention including, but not limited to, Aromatic Fire-cured, Brightleaf tobacco, Burley; Cavendish; Corojo; Criollo; Oriental Tobacco; Perique; Shade tobacco; Thuoc lao; Type 22; NC95, K326, K346, White Burley, Wild Tobacco, Y1, and the like.

As used herein, the term "nucleotide, sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. All nucleic acids provided herein have 5' and 3' ends. Further, except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

The term "plant part," as used herein, includes but is not limited to reproductive tissues (e.g., petals, sepals, stamens, pistils, receptacles, anthers, pollen, flowers, fruits, flower bud, ovules, seeds, embryos); vegetative tissues (e.g., petioles, stems, roots, root hairs, root tips, pith, coleoptiles, stalks, shoots, branches, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

"Plant cell culture" means cultures of plant units such as, for example, protoplasts, cell culture cells, cells in plant tissues, pollen, pollen tubes, ovules, embryo sacs, zygotes and embryos at various stages of development. In some embodiments of the invention, a transgenic tissue culture or transgenic plant cell culture is provided, wherein the transgenic tissue or cell culture comprises a nucleic acid molecule/nucleotide sequence of the invention.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount. Thus, for example, reduced transcription of a target DNA can mean a reduction in the transcription of the target gene of at least about 30%, 35%, 40%, 45%, 50%, 55%, 60%, 65%, 70%, 75%, 80%, 85%, 90%, 95%, 96%, 97%, 98%, 99%, or 100% as compared to a control (e.g., a plant not comprising the mutation in the BBL nucleic acids).

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data*, Part I (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, a "target DNA," "target region" or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a region of a gene against which any class of custom designed nuclease (e.g., ZFN, TALEN, meganuclease, CRISPR-Cas and the like) has been engineered to bind and cleave.

As used herein, the phrase "substantially identical," or "substantial identity" in the context of at least two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection.

For sequence comparison, typically one sequence acts as a reference sequence to which test sequences are compared.

When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen Laboratory Techniques in *Biochemistry and Molecular Biology-Hybridization with Nucleic Acid Probes* part I chapter 2 "Overview of principles of hybridization and the strategy of nucleic acid probe assays" Elsevier, N.Y. (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

In any of the embodiments described herein, the nucleotide sequences of interest (e.g., nucleic acids encoding nucleases useful for mutating BBL nucleic acids) can be operably associated with a variety of promoters, terminators, and/or other regulatory elements for expression in plant cell. Any promoter, terminator or other regulatory element functional in a plant cell may be used with the nucleic acids of this invention. In representative embodiments, a promoter may be operably linked to a polynucleotide and/or nucleic acid useful in carrying out the invention. In some embodiments, a terminator may be operably linked to a polynucleotide and/or nucleic acid of the invention.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II or RNA polymerase III and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art. The choice of promoter will vary depending on the temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate. In some embodiments, expression of a nucleotide sequence of interest can be in any plant and/or plant part, (e.g., in leaves, in stalks or stems, in ears, in inflorescences, in roots, seeds and/or seedlings, and the like) and the promoter is selected accordingly.

In embodiments described herein, one or more of the polynucleotides and nucleic acids of the invention may be operably associated with a promoter as well as a terminator, and/or other regulatory elements for expression in plant cell. Any promoter, terminator or other regulatory element that is functional in a plant cell may be used with the nucleic acids of this invention. Non-limiting examples of promoters useful with this invention include an *Arabidopsis thaliana* U6 RNA polymerase III promoter, a 35S promoter, actin promoter, ubiquitin promoter, Rubisco small subunit promoter, an inducible promoter, including but not limited to, a an AlcR/AlcA (ethanol inducible) promoter, a glucocorticoid receptor (GR) fusion, GVG, a pOp/LhGR (dexamethasone inducible) promoter, a XVE/OlexA (β-estradiol inducible) promoter, a heat shock promoter and/or a bidirectional promoter (See, e.g., Gatz, Christine. *Current Opinion in Biotechnology* 7(2):168-172 (1996); Borghi L. Methods Mol Biol.655:65-75(2010); Baron et al. *Nucleic acids research* 23(17) (1995), 3605; Kumar et al. *Plant molecular biology* 87(4-5):341-353 (2015)).

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

In some embodiments, the components for modifying or mutating a BBL nucleic acid and any other polynucleotide of interest (e.g., other polynucleotides encoding nicotinic alkaloid biosynthetic enzymes transcription factors that positively regulate nicotinic alkaloid biosynthesis) may be comprised in an "expression cassette." As used herein, "expression cassette" means a nucleic acid construct comprising a nucleotide sequence of interest (e.g., a nuclease useful for mutating a BBL nucleic acid), wherein said nucleotide sequence is operatively associated with at least a control sequence (e.g., a promoter). An expression cassette may be chimeric, meaning that at least one of its components is heterologous with respect to at least one of its other components. Thus, for example, the nucleic acids to be expressed may be operably linked to a promoter or other regulatory element that is heterologous to the nucleic acids to be expressed (e.g., heterologous to a CRISPR guide DNA). An expression cassette may also be one that is naturally occurring but has been obtained in a recombinant form useful for heterologous expression.

In addition to promoters, an expression cassette also can optionally include additional regulatory elements functional in a plant cell including, but not limited to, a transcriptional and/or translational termination region (i.e., termination region). A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). Non-limiting examples of terminators functional in a plant and useful with this invention include an actin terminator; a Rubisco small subunit terminator, a Rubisco large subunit terminator, a nopaline synthase terminator, and/or a ubiquitin terminator.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acids described herein can be used in connection with vectors. The term "vector" refers to a composition for transferring, delivering or introducing one or more nucleic acids into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms. In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the polynucleotides and/or expression cassettes can be comprised in vectors as described herein and as known in the art.

"Introducing," "introduce," "introduced" (and grammatical variations thereof) in the context of a polynucleotide of interest (e.g., a nuclease useful for mutating a BBL nucleic acid) means presenting the polynucleotide of interest to the host organism or cell of said organism (e.g., host cell) in such a manner that the polynucleotide gains access to the interior of a cell. Where more than one polynucleotide is to be introduced these polynucleotides can be assembled as part of a single polynucleotide or nucleic acid construct, or as separate polynucleotides or nucleic acid constructs, and can be located on the same or different expression constructs or transformation vectors. Accordingly, these polynucleotides can be introduced into cells in a single transformation event, in separate transformation/transfection events, or, for example, they can be incorporated into an organism by conventional breeding protocols. Thus, in some aspects, one or more polynucleotides encoding nucleases useful for modifying or mutating a BBL nucleic acid (e.g., Crispr-Cas nucleases, meganucleases, zinc finger nucleases (ZFNs), and/or transcription activator-like effector nucleases (TALENs)) can be introduced singly or in combination in a single expression cassette and/or vector into a host organism or a cell of said host organism.

The term "transformation" or "transfection" as used herein refers to the introduction of a heterologous nucleic acid into a cell, such as a nucleic acid encoding a nuclease. Transformation of a cell may be stable or transient or may be in part stably transformed and in part transiently transformed. Thus, in some embodiments, the modifications to the plant genome can be stable and in some embodiments, the modifications can be transient. In some embodiments, after stable transformation, the nucleic acid constructs introduced to the plant genome can be removed by, for example, crossing with non-modified plants or segregation of non-homozygous plants.

"Transient transformation" in the context of a polynucleotide means that a polynucleotide is introduced into the cell and does not integrate into the genome of the cell.

By "stably introducing" or "stably introduced," in the context of a polynucleotide, means that the introduced polynucleotide is stably incorporated into the genome of the cell, and thus the cell is stably transformed with the polynucleotide.

"Stable transformation" or "stably transformed" as used herein means that a nucleic acid construct is introduced into a cell and integrates into the genome of the cell. As such, the integrated nucleic acid construct is capable of being inherited by the progeny thereof, more particularly, by the progeny of multiple successive generations. "Genome" as used herein can include the nuclear, plastid, and/or mitochondrial genome, and therefore may include integration of a nucleic acid construct into the nuclear, plastid and/or mitochondrial genome. Stable transformation as used herein may also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into a plant or plant cell. Stable transformation of a cell can be detected by, for example, a Southern blot hybridization assay of genomic DNA of the cell with nucleic acid sequences which specifically hybridize with a nucleotide sequence of a transgene introduced into an organism (e.g., a bacterium, an archaea, a yeast, an algae, and the like). Stable transformation of a cell can be detected by, for example, a Southern blot hybridization assay of DNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Thus, in particular embodiments of the invention, intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

As used herein, "tobacco product" refers to a product comprising material produced by a *Nicotiana* plant, including for example, nicotine gum and patches for smoking cessation, cigarette tobacco including expanded (puffed) and reconstituted tobacco, cigar tobacco, pipe tobacco, cigarettes, cigars, and all forms of smokeless tobacco such as chewing tobacco, snuff, snus and lozenges. "Cigarettes" includes electronic cigarettes and "heat not burn" products which are cigarette-like devices that heat tobacco rather than burn tobacco.

The present invention is directed in part to the discovery that modifying polynucleotides encoding BBLe, BBLd-1 or BBLd-2 so as to reduce or eliminate expression and/or activity of the polynucleotides and/or any polypeptide produced can result in the plant having reduced nicotinic alkaloid content as compared to a plant that does not comprise said modification.

Since the 1930s, tobacco researchers have been engaged in altering tobacco genetics to affect the levels of nicotine and other alkaloids. Large reductions in tobacco alkaloid levels have historically been achieved through the use of naturally-occurring recessive alleles at the Nic1 and Nic2 loci (also designated as the A and B loci, in some literature). Recessive alleles at both of these loci can reduce alkaloid levels from between 1.5% and 4.5% total dry weight to as low as approximately 0.2% (Legg et al., 1969; Legg and Collins, 1971; Chaplin and Weeks, 1976). Although the Nic1 locus remains uncharacterized, the Nic2 locus was recently shown to encode for a cluster of transcription factors of the ethylene response factor (ERF) gene family (Shoji et al., 2010). However, tobacco varieties carrying the recessive nic1 or nic2 alleles have not been widely used due to negative associations with yield and quality (Legg et al., 1970; Chaplin and Weeks, 1976; Chaplin and Burk, 1983). The negative attributes of tobacco plants homozygous for the mutant nic1 and nic2 loci are likely a result of the fact that they not only influence the expression of genes involved in alkaloid biosynthesis but an array of unrelated genes as well (Kidd et al., 2006).

A great deal of knowledge has been gained over the last twenty years regarding the molecular biology underlying the biosynthesis of tobacco alkaloids (reviewed by Dewey and Xie, 2013). As the genes encoding specific steps of nicotine biosynthesis have been elucidated, these have become targets for reducing the nicotine content of the plant. Although it has been shown that transgene mediated down-regulation of several steps in the alkaloid biosynthetic pathway can result in reduced nicotine accumulation, most of these perturbations are accompanied by undesirable side-effects, such as reduced growth, or the concomitant increase in the levels of the typically minor alkaloid anatabine (reviewed in Dewey and Xie, 2013). In tobacco, enzymes referred to as berberine bridge enzyme-like (BBL) proteins catalyze one of last steps of alkaloid biosynthesis (Kajikawa et al., 2011). Our research to date on this gene family, summarized below, has shown that this specific step of the alkaloid biosynthetic pathway is a particularly attractive target for the development of high quality, low alkaloid tobaccos.

Thus, in some embodiments of the invention, a method of producing a *Nicotiana* plant or plant part having reduced nicotinic alkaloid content is provided, comprising, consisting essentially of, or consisting of introducing into a *Nicotiana* plant or plant part (a) a mutation in an endogenous BBLe polynucleotide having 97% identity to the nucleotide sequence of SEQ ID NO:3, (b) a mutation in an endogenous BBLd-1 polynucleotide having 97% identity to the nucleotide sequence of SEQ ID NO:1, and/or (c) a mutation in an endogenous BBLd-2 polynucleotide having 97% identity to the nucleotide sequence of SEQ ID NO:2, thereby producing a *Nicotiana* plant or plant part having reduced nicotinic alkaloid content as compared to a control *Nicotiana* plant or plant part that does not comprise the mutation of (a), (b), or (c). In some embodiments, the at least one recombinant nucleic acid may be stably incorporated into the genome of the plant, which is then removed from the genome of the plant by backcrossing the transgenic *Nicotiana* plant with a *Nicotiana* plant not comprising the at least one recombinant nucleic acid. In some embodiments, introducing comprises introducing the mutation into a plant cell and regenerating the plant cell into a plant, thereby producing a plant having reduced nicotinic alkaloid content. In other embodiments, the method further comprises selecting a *Nicotiana* plant or plant part comprising (a) a mutation in the BBLe nucleotide sequence having at least 97% identity to the nucleotide sequence of SEQ ID NO:3, (b) a mutation in the BBLd-1 polynucleotide sequence having at least 97% identity to the nucleotide sequence of SEQ ID NO:1 (BBLd-1), and/or (c) a mutation in the BBLd-2 polynucleotide sequence having at least 97% identity to the nucleotide sequence of SEQ ID NO:2 (BBLd-2). In some embodiments, the nicotinic alkaloid comprises, consists essentially of, or consists of nicotine.

In some embodiments, a method of reducing nicotinic alkaloid content in a *Nicotiana* plant or plant part is provided, comprising, consisting essentially of, or consisting of introducing into a *Nicotiana* plant or plant part (a) a mutation in an endogenous BBLe polynucleotide having 97% identity to the nucleotide sequence of SEQ ID NO:3, (b) a mutation in an endogenous BBLd-1 polynucleotide having 97% identity to the nucleotide sequence of SEQ ID NO:1, and/or (c) a mutation in an endogenous BBLd-2 polynucleotide having 97% identity to the nucleotide sequence of SEQ ID NO:2, thereby producing a *Nicotiana* plant or plant part having reduced nicotinic alkaloid content as compared to a control *Nicotiana* plant or plant part that does not comprise the mutation of (a), (b), or (c). In some embodiments, the at least one recombinant nucleic acid may be stably incorporated into the genome of the plant, which is then removed from the genome of the plant by backcrossing the plant with a plant not comprising the at least one recombinant nucleic acid. In further embodiments, introducing comprises introducing the mutation into a plant cell and regenerating the plant cell into a plant or plant part, thereby producing a plant or plant part having reduced nicotinic alkaloid content. In other embodiments, the method further comprises selecting a *Nicotiana* plant or plant part comprising (a) a mutation in the BBLe nucleotide sequence having at least 97% identity to the nucleotide sequence of SEQ ID NO:3, (b) a mutation in the BBLd-1 polynucleotide sequence having at least 97% identity to the nucleotide sequence of SEQ ID NO:1 (BBLd-1), and/or (c) a mutation in the BBLd-2 polynucleotide sequence having at least 97% identity to the nucleotide sequence of SEQ ID NO:2 (BBLd-2). In some embodiments, the nicotinic alkaloid comprises, consists essentially of, or consists of nicotine.

Procedures for determining nicotinic alkaloid content are well known and routine in the art and are described throughout the literature. Non-limiting examples of such methods include gas chromatography, mass spectrometry (Domino et al. 1992 *Med Sci Res.* 20:859-860; Sheen et al. 2006 *J Food Sci* 53(5):1572-1573), HPLC (Keinänen et al. 2001 *J Agric Food Chem* 49:3553-3558; Halitschke and Baldwin 2003 *Plant J*36: 794-807), UV absorption (Willits et al. 2005 *Analytical Chemistry* 22:430-433), and the like.

In some embodiments, a mutation may reduce or eliminate expression of (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2. In some embodiments, a mutation may reduce or eliminate activity of (a) a polypeptide encoded by the BBLe polynucleotide having 97% identity to the nucleotide sequence of SEQ ID NO:3, (b) a polypeptide encoded by the BBLd-1 polynucleotide having 97% identity to the nucleotide sequence of SEQ ID NO:1, and/or (c) a polypeptide encoded by the BBLd-2 polynucleotide having 97% identity to the nucleotide sequence of SEQ ID NO:2. In representative embodiments, expression of a BBLe, BBLd-1, BBLd-2 polynucleotide and/or the activity of a BBLe, BBLd-1, BBLd-2 polypeptide may be reduced by at least about 30% (e.g., about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range or value therein).

Introducing a mutation may comprise, consist essentially of, or consist of in planta modification of one or more of the wild-type or native nucleotide sequences encoding the BBL polynucleotides of this invention (e.g., a BBLe polynucleotide having 97% identity to the nucleotide sequence of SEQ ID NO:3, a BBLd-1 polynucleotide having 97% identity to the nucleotide sequence of SEQ ID NO:1, and/or (c) a BBLd-2 polynucleotide having 97% identity to the nucleotide sequence of SEQ ID NO:2). Any method of modify a nucleotide sequence in planta can be used with this invention to alter the expression of the genes encoding these BBL polynucleotides. Thus, in some embodiments, introducing a mutation into a *Nicotiana* plant may comprise, consist essentially of, or consist of chemical mutagenesis, insertional mutagenesis and/or irradiation of the plant or a plant part. Non-limiting examples of chemical mutagens include ethylmethane sulfonate (EMS), nitrosoguanidine, bisulfite, $N^4$-hydroxycytidine, and/or aminopurine. Non-limiting examples of irradiation mutagens include gamma-ray, x-ray, and/or fast neutron irradiation. Insertional mutagenesis techniques include but are not limited to T-DNA tagging, transposon tagging and mutagenic oligonucleotides. In representative embodiments, the mutation may be a deletion or an insertion, optionally a deletion or insertion that results in a net loss or gain of nucleotides that is not divisible by three, thereby generating a frameshift mutation that may result in a nonfunctional protein, if a protein is produced at all.

In some embodiments, introducing the mutation into a *Nicotiana* plant or plant part comprises introducing into the *Nicotiana* plant or plant part at least one recombinant nucleic acid encoding a nuclease targeting (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (b) a BBLd-2 polynucleotide having 97% identity to the nucleotide sequence of SEQ ID NO:2. In some embodiments, the introduction of the recombinant nucleic acid can be stable or transient. In some embodiments, when the introduction is stable, the introduced constructs (e.g., the at least one recombinant nucleic acid) can be removed, for example, by crossing the transformed plant with non-modified plants or through segregation of non-homozygous plants. Non-limiting examples of a nuclease useful for generating mutants in an endogenous BBL polynucleotide of the invention includes a meganuclease, a zinc finger nuclease (ZFN), a transcription activator-like effector nuclease (TALEN), and/or a clustered regularly interspaced, short palindromic repeat (CRISPR) associated (Cas) nuclease. Use of such nucleases for creating targeted mutations is well known in the art and routine. In representative embodiments, the mutation may be a deletion or an insertion, optionally a deletion or insertion resulting in a net loss or gain of nucleotides that is not divisible by three, thereby generating a frameshift mutation that may result in a nonfunctional protein, if a protein is produced at all.

Meganucleases, endodeoxyribonucleases, or homing enzymes comprise recognition sites of from about 12-40 base pairs of double stranded DNA. These large recognition sites make these nucleases very specific for their target site. Exemplary meganucleases useful in genome modification include I-SceI, I-DmoI, and I-CreI. In some embodiments, a meganuclease may be modified to alter the portion of the amino acid sequence of the meganuclease that recognizes the target DNA, thereby generating meganucleases that recognize different DNA sequences (see, e.g., U.S. Pat. No. 8,021,867). Use of meganucleases for targeted DNA modification of gene sequences is well known in the art (see, Stoddard, B. L. *Quarterly Reviews of Biophysics* 38(1):49-95 (2006), doi:10.1017/S0033583505004063; Arnould et al. *Journal of Molecular Biology* 355(3):443-58 (2006). doi: 10.1016/j.jmb.2005.10.065; Delacôte et al. PloS One 8(1): e53217 (2013-01-01). doi:10.1371/journal.pone.0053217; de Souza, N., *Nat Meth* 9 (1), 27-27 (2011); and Antunes et al. *BMC Biotechnology* 12:86 (2012)). Thus, in some embodiments, when the nuclease is a meganuclease, the target region can be about 12 to about 40 consecutive base pairs in length (e.g., about 12, 13, 14, 15, 16, 17, 18, 19, 20, 21, 22, 23, 24, 25, 26, 27, 28, 29, 30, 31, 32, 33, 34, 35, 36, 37, 38, 39, 40 consecutive base pairs, or any range or value therein) from a BBLe polynucleotide having 97% identity to the nucleotide sequence of SEQ ID NO:3, a BBLd-1 polynucleotide having 97% identity to the nucleotide sequence of SEQ ID NO:1, or a BBLd-2 polynucleotide having 97% identity to the nucleotide sequence of SEQ ID NO:2. In exemplary embodiments, the target region can be about 14 to 40 consecutive base pairs in length, about 15 to about 35 consecutive base pairs in length, about 18 to about 30 consecutive base pairs in length, or about 20 to about 30 consecutive base pairs in length. In particular embodiments, the target region can be about 22 consecutive base pairs in length. In some embodiments, the nuclease can be I-CreI meganuclease.

Zinc finger nucleases (ZFNs) are chimeric proteins comprising at least one zinc finger DNA binding domain linked to at least one nuclease capable of cleaving DNA. Exemplary nucleases useful in a ZFN are FokI restriction enzymes. (Urnov et al. *Nature Reviews Genetics* 11, 636-646 (2010)). Zinc finger binding domains can be "engineered" to bind to a predetermined nucleotide sequence (See, for example, Id., U.S. Pat. Nos. 6,140,081; 6,453,242; and 6,534,261; see also WO 98/53058; WO 98/53059; WO 98/53060; WO 02/016536 and WO 03/016496. Cleavage by a ZFN at a target nucleic acid typically results in a double stranded break at the target site. Notably, ZFNs are unique in that their DNA target sites will always be divisible by 3. In some embodiments, the DNA target site can range from about 9 consecutive base pairs to about 30 consecutive base pairs in length (e.g., about 9, 10, 11, 12, 13, 14, 15, 16, 17, 18, 19, 20, 21, 22, 23, 24, 25, 26, 27, 28, 29, 30 base pairs in length). Accordingly, in some embodiments, the target site for a ZFN can be about 9 consecutive base pairs to about 30 consecutive base pairs (or any range or value therein) from a BBLe polynucleotide having 97% identity to the nucleotide sequence of SEQ ID NO:3, a BBLd-1 polynucleotide having 97% identity to the nucleotide sequence of SEQ ID NO:1, or a BBLd-2 polynucleotide having 97% identity to the nucleotide sequence of SEQ ID NO:2

Transcription activator-like effector nucleases (TALENs) are chimeric proteins comprising FokI nucleases fused with transcription activator like proteins (TAL) (i.e., TAL effector DNA binding domain). TAL proteins are composed of 33-35 amino acid repeating motifs with variable positions that have a strong recognition for specific nucleotides (Deng et al. *Protein Cell* 5(4):297-306 (2014)) (approximately 10-30 repeat units per binding domain). One specific DNA base is recognized through a highly variable residue at a fixed position in the TAL repeat. Each TALEN fusion thus provides a TALEN monomer consisting of a TAL effector DNA binding domain with a Fok1 catalytic domain fused to its C terminus. Since FokI cleaves as a dimer, the TAL effector nucleases function in pairs, binding opposing DNA target sites across a gap located between the target sites over which the FokI domains come together to create the break. Thus, a pair of TALENs bind to candidate target sites oriented from 5' to 3' on opposite strands of DNA having a spacer region between the sites, wherein the spacer region is large enough for the two Fok1 domains to dimerize and cut the DNA, but not so large that the two Fok1 domains do not come into contact (Cermak et al. *Nucleic Acids Res.* 39(12): e82 (2011)). Methods for making and using TALENs for DNA modification are well known and routine in the art (see, e.g., U.S. Pat. Nos. 8,440,432; 8,507,272; 8,912,138; Miller, J. C. et al. *Nat. Biotechnol.* 29, 143-148 (2011); and Christian, M. et al. *Genetics* 186, 757-761 (2010)). In some embodiments, a DNA target site for TALEN can range from about 9 consecutive base pairs to about 40 consecutive base pairs in length (e.g., about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 base pairs in length). Accordingly, in some embodiments, the target site for a ZFN can be about 9 consecutive base pairs to about 40 consecutive base pairs (or any range or value therein) from a BBLe polynucleotide having 97% identity to the nucleotide sequence of SEQ ID NO:3, a BBLd-1 polynucleotide having 97% identity to the nucleotide sequence of SEQ ID NO:1, or a BBLd-2 polynucleotide having 97% identity to the nucleotide sequence of SEQ ID NO:2.

Clustered regularly interspaced, short palindromic repeat (CRISPR) associated (Cas) nucleases are also useful for modifying endogenous BBL polynucleotides. In contrast to TALENS, ZFNs and homing meganucleases, newly engineered CRISPR-Cas nucleases are not required for each use. The requirements for cleavage and DNA modification using CRISPR-Cas systems are well known and routine. (U.S. Pat. Nos. 8,906,616; 8,895,308; 8,993,233; Jiang et al. 2013. *Nat. Biotechnol.* 31:233-239; Briner et al. Mol. Cell 56:333-339 (2014); Cong et al. *Science* 339:819-823 (2013); Gilbert et al. *Cell* 154: 442-451 (2013); Jinek et al. *Science* 337: 816-821 (2012); Qi et al. Cell 152:1173-1183 (2013); Ran et al. *Nature Protocols* 8:2281-2308 (2013); and Sander et al. *Nat. Biotechnol* 32, 347-355 (2014)). Type II CRISPR systems are the monst commonly used for genome editing. The bacterial Type II CRISPR systems comprise two RNA components, a CRISPR RNA (crRNA) and a transactivating RNA (tracrRNA). To facilitate use in genome engineering applications, these two RNA components may be combined into a single RNA that is referred to as a guide RNA (gRNA or sgRNA). The most commonly used genome engineering system is the CRISPR-Cas9 system derived from *Streptococcus pyogenes*.

For successful cleavage, a guide RNA is designed to comprise a "recognition motif" that is complementary to a target DNA sequence (protospacer) that is next to (e.g., immediately downstream of) a "protospacer adjacent motif" (PAM) sequence. In some embodiments, the PAM sequence may be NGG. In some embodiments, a recognition motif of a gRNA for a CRISPR-Cas system can comprise a sequence having length of about 10 consecutive base pairs to about 30 consecutive base pairs (e.g., about 10, 11, 12, 13, 14, 15, 16, 17, 18, 19, 20, 21, 22, 23, 24, 25, 26, 27, 28, 29, 30 consecutive base pairs, and any range or value therein) that is complementary to a target DNA (protospacer) (e.g., to a BBLe polynucleotide having 97% identity to the nucleotide sequence of SEQ ID NO:3, a BBLd-1 polynucleotide having 97% identity to the nucleotide sequence of SEQ ID NO:1, or a BBLd-2 polynucleotide having 97% identity to the nucleotide sequence of SEQ ID NO:2). In some embodiments, the spacer comprises a length of about 15 to about 30, about 15 to about 25, about 15 to about 20, about 18 to about 30, about 18 to about 25, about 18 to about 20, about 20 to about 30, about 25 to about 30, and the like, consecutive base pairs having complementarity to a target DNA. In some embodiments, two gRNA constructs positioned in close proximity and opposite orientation (like the two monomers of a TALENs) may be generated and used with Cas9 nucleases having a single nickase activity. Such a design may increase target specificity. In some embodiments, the nickase activity of the Cas9 may be inactivated and the Cas9 fused to Fok1 nuclease (fCas9) so that the Fok1 nuclease only functions when two fCas9 "monomer" units dimerize. Again, such a design may increase target specificity. (Guilinger et al. *Nature Biotechnol.* 32:577-588(2014))

In some embodiments, the invention further comprises reducing the activity of at least one additional nicotinic alkaloid biosynthetic enzyme and/or reducing the expression of a polynucleotide encoding at least one additional nicotinic alkaloid biosynthetic enzyme in a *Nicotiana* plant or plant part. Thus, in some embodiments, in addition to introducing into a *Nicotiana* plant or plant part a mutation in at least one of an endogenous BBLe polynucleotide having 97% identity to the nucleotide sequence of SEQ ID NO:3, a mutation in an endogenous BBLd-1 polynucleotide having 97% identity to the nucleotide sequence of SEQ ID NO:1, and/or a mutation in an endogenous BBLd-2 polynucleotide having 97% identity to the nucleotide sequence of SEQ ID NO:2, the *Nicotiana* plant or plant part may be further modified so as to reduce the activity of additional nicotinic alkaloid biosynthetic enzymes or reduce the expression of nucleic acids encoding the additional nicotinic alkaloid biosynthetic enzymes. Such additional nicotinic alkaloid biosynthetic enzymes include but are not limited to additional berberine bridge enzyme-like polypeptide (e.g., BBLa, BBLb, BBLc), aspartate oxidase, quinolinate synthase, quinolate phosphoribosyl transferase, ornithine decarboxylase, putrescine N-methyltransferase, methyl putrescine oxidase, and A622. Thus, for example, in addition to introducing into a *Nicotiana* plant or plant part a mutation in at least one of an endogenous BBLe polynucleotide having 97% identity to the nucleotide sequence of SEQ ID NO:3, a mutation in an endogenous BBLd-1 polynucleotide having 97% identity to the nucleotide sequence of SEQ ID NO:1, and/or a mutation in an endogenous BBLd-2 polynucleotide having 97% identity to the nucleotide sequence of SEQ ID NO:2, the *Nicotiana* plant or plant part may be further modified so as to reduce the expression of BBLa, BBLb, and/or BBLc and/or reduce the activity of an additional berberine bridge enzyme-like polypeptide such as BBLa, BBLb, and/or BBL. In some embodiments, in addition to introducing into a *Nicotiana* plant or plant part a mutation in at least one of an endogenous BBLe polynucleotide having 97% identity to the nucleotide sequence of SEQ ID NO:3, a mutation in an endogenous BBLd-1 polynucleotide having 97% identity to the nucleotide sequence of SEQ ID NO:1, and/or a mutation in an endogenous BBLd-2 polynucleotide having 97% identity to the nucleotide sequence of SEQ ID NO:2, the *Nicotiana* plant or plant part may be further modified to reduce the expression of BBLa, BBLb, and/or BBLc and/or reduce the activity of an additional berberine bridge enzyme-like polypeptide such as BBLa, BBLb, and/or BBL, wherein the modification to reduce the expression of BBLa, BBLb, and/or BBLc or the activity of BBLa, BBLb, and/or BBL comprises, consists essentially of, or consists of an ethyl methanesulfonate (EMS) mutation of a nucleotide sequence encoding BBLa, BBLb, and/or BBLc.

In some embodiments, the invention further comprises reducing expression of a polynucleotide encoding a transcription factor that positively regulates nicotinic alkaloid biosynthesis in a *Nicotiana* plant or plant part. Thus, in some embodiments, in addition to introducing into a *Nicotiana* plant or plant part a mutation in at least one of an endogenous BBLe polynucleotide having 97% identity to the nucleotide sequence of SEQ ID NO:3, a mutation in an endogenous BBLd-1 polynucleotide having 97% identity to the nucleotide sequence of SEQ ID NO:1, and/or a mutation in an endogenous BBLd-2 polynucleotide having 97% identity to the nucleotide sequence of SEQ ID NO:2, a *Nicotiana* plant or plant part may be further modified to reduce expression of at least one polynucleotide encoding a transcription factor that positively regulates nicotinic alkaloid biosynthesis. Non-limiting examples of transcription factors that positively regulate nicotinic alkaloid biosynthesis include ERF family transcription factors such as ERF189, ERF221 and ERF32, and/or bHLH family transcription factors such as NtMYC1 and NtMYC2, and COI1.

In some embodiments, the invention further comprises overexpression of at least one polynucleotide encoding a transcription factor that negatively regulates nicotinic alkaloid biosynthesis in a *Nicotiana* plant or plant part. Thus, in some embodiments, in addition to introducing into a *Nicotiana* plant or plant part a mutation in at least one of an endogenous BBLe polynucleotide having 97% identity to the nucleotide sequence of SEQ ID NO:3, a mutation in an endogenous BBLd-1 polynucleotide having 97% identity to the nucleotide sequence of SEQ ID NO:1, and/or a mutation in an endogenous BBLd-2 polynucleotide having 97% identity to the nucleotide sequence of SEQ ID NO:2, a *Nicotiana* plant or part thereof may be further modified to overexpress at least one polynucleotide encoding a transcription factor that negatively regulates nicotinic alkaloid biosynthesis. Non-limiting examples of transcription factors that negatively regulate nicotinic alkaloid biosynthesis includes JAZ.

As used herein, "overexpress," "overexpression," overexpressed, (and grammatical variations thereof) refer to the production of a gene product in a transgenic *Nicotiana* plant or plant part that exceeds the level of production of the same gene product in a control *Nicotiana* plant or plant part, the transgenic *Nicotiana* plant or plant part being transformed with a recombinant nucleic acid construct that confers the increased production of the gene product, whereas the control *Nicotiana* plant or plant part is not transformed with said recombinant nucleic acid construct.

The expression and activity of any of additional polynucleotides to be altered in a *Nicotiana* plant or plant part of this invention may be reduced by introducing mutations as described herein for BBLe, BBLd-1, BBLd-2, or may be reduced by other well known means of reducing expression of polynucleotides and activity of polypeptides including but not limited to use of interfering RNAs developed from the nucleic acids encoding the additional nicotinic alkaloid biosynthetic enzymes. As is well known in the art, "interfering RNA" is RNA capable of causing gene silencing. Interfering RNA, as used herein, includes any type of RNA molecule capable of down-regulating or silencing expression of a target nicotinic alkaloid biosynthetic nucleic acid, including but not limited to sense RNA, antisense RNA, short interfering RNA (siRNA), microRNA (miRNA), double-stranded RNA (dsRNA), hairpin RNA (RNA) and the like.

In additional embodiments, the invention further provides a *Nicotiana* plant and/or plant part comprising reduced nicotinic alkaloid content produced by any of the methods of the invention. In some embodiments, the *Nicotiana* plant part may be a *Nicotiana* plant cell. Thus, in some embodiments, the invention provides a *Nicotiana* plant or plant part of the invention having reduced nicotinic alkaloid content and comprising, consisting essentially of, or consisting of a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2. In some embodiments, the mutation may be a deletion or insertion mutation. In some embodiments, the expression of the BBLe polynucleotide having 97% identity to the nucleotide sequence of SEQ ID NO:3 may be reduced by about 30% to about 100%, the expression of the BBLd-1 polynucleotide having 97% identity to the nucleotide sequence of SEQ ID NO:1may be reduced by about 30% to about 100%, and/or the expression of the BBLd-2 polynucleotide having 97% identity to the nucleotide sequence of SEQ ID NO:2 may be reduced by about 30% to about 100%. In some embodiments, the activity of a polypeptide produced by the BBLe polynucleotide having 97% identity to the nucleotide sequence of SEQ ID NO:3 may be reduced by about 30% to about 100%, the activity of a polypeptide produced by the BBLd-1 polynucleotide having 97% identity to the nucleotide sequence of SEQ ID NO:1may be reduced by about 30% to about 100%, and/or the activity of a polypeptide produced by the BBLd-2 polynucleotide having 97% identity to the nucleotide sequence of SEQ ID NO:2 may be reduced by about 30% to about 100%. In some embodiments, the *Nicotiana* plant or plant part may further comprise (1) reduced activity and/or reduced expression of at least one additional nicotinic alkaloid biosynthetic polypeptide or polynucleotide, respectively, and/or (2) reduced expression of a encoding a transcription factor that positively regulates nicotinic alkaloid biosynthesis, and/or (3) increased expression (overexpression) of a encoding a transcription factor that negatively regulates nicotinic alkaloid biosynthesis.

In some embodiments, the nicotine content of a *Nicotiana* plant or plant part of the invention (e.g., having at least reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2) can be about 10 mg/g (e.g., about 1%) to about 100 mg/g (e.g., 10%) (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 mg/g, and any range or value therein) dry weight nicotine. In particular embodiments, the nicotine content of a *Nicotiana* plant or plant part of the invention can be about 20 mg/g (e.g., about 2%) to about 100 mg/g (e.g., 10%) dry weight nicotine; about 30 mg/g to about 100 mg/g dry weight nicotine, about 40 mg/g to about 100 mg/g dry weight nicotine, about 50 mg/g to about 100 mg/g dry weight nicotine, and the like. In still other embodiments, the nicotine content of a *Nicotiana* plant or plant part of the invention can be at least about 30 mg/g dry weight nicotine, at least about 40 mg/g (e.g., about 4%) dry weight nicotine, at least about 50 mg/g (e.g., about 5%) dry weight nicotine, at least about 60 mg/g (e.g., about 6%) dry weight nicotine, and the like. In some embodiments, the nicotine content can be reduced to less than 10 mg/g (e.g., 10, 9, 8, 7, 6, 5, 4, 3, 2, 1, 0 mg/g nicotine)

In some embodiments, a *Nicotiana* seed of a plant of the invention and *Nicotiana* plants produced from the seed are provided, wherein the seed comprises a mutation in the BBLe polynucleotide having 97% identity to the nucleotide sequence of SEQ ID NO:3, a mutation in the BBLd-1 polynucleotide having 97% identity to the nucleotide sequence of SEQ ID NO:1, and/or a mutation in the BBLd-2 polynucleotide having 97% identity to the nucleotide sequence of SEQ ID NO:2.

In some embodiments, the invention provides a progeny *Nicotiana* plant produced from the *Nicotiana* plants of the invention. In some embodiments, further provided is a crop comprising a plurality of *Nicotiana* plants of the invention planted together in an agricultural field.

Additional aspects of the invention include a harvested product produced from the *Nicotiana* plants or plant parts of the invention, as well as a processed product produced from said harvested product. A harvested product can be a whole plant or any plant part, wherein said harvested product comprises a recombinant nucleic acid molecule/construct of the invention. Thus, in some embodiments, non-limiting examples of a harvested product include a seed, a fruit, a flower or part thereof (e.g., an anther, a stigma, and the like), a leaf, a stem, and the like.

In some embodiments, the present invention provides a tobacco product, wherein the product can be a blended tobacco product. In other embodiments of the invention, the tobacco product of the present invention can be a reduced nicotine tobacco product. In still other embodiments, the tobacco product of the present invention can be a blended tobacco product with reduced nicotine content. Thus, the tobacco product of the present invention can be a blended reduced nicotine tobacco product.

In some embodiments, a tobacco product may include, but is not limited to, leaf tobacco, shredded tobacco, cut tobacco, ground tobacco, powder tobacco, tobacco extract, smokeless tobacco, moist or dry snuff, kretek, pipe tobacco, cigar tobacco, cigarillo tobacco, cigarette tobacco, chewing tobacco, cigarettes, cigars, bidis, bits, and tobacco-containing gum and lozenges. In particular embodiments, the tobacco product may be a cigarillo, a non-ventilated recess filter cigarette, a vented recess filter cigarette, a cigar, snuff, and chewing tobacco. In some embodiments, the tobacco product may be produced from a form of tobacco including but not limited to leaf tobacco, shredded tobacco, cut tobacco, ground tobacco, powder tobacco, tobacco extract, and any combination thereof. In some embodiments, a tobacco product of the invention comprises a blended tobacco product, a reduced nicotine tobacco product, and any combination thereof.

Those of skill in the art understand that tobacco plants, or parts thereof, are traditionally cured prior to use in a tobacco product. Thus, additional embodiments of the present invention include tobacco products comprising cured tobacco made from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2. Accordingly, tobacco plants and plant parts can be cured accordingly to processes known to those of skill in the art. Such processes include, but are not limited to, air curing, ground curing, rack curing, pit curing, fire curing, sun curing and flue curing.

The present invention further provides a method of producing a tobacco product, comprising providing a cured tobacco, wherein the cured tobacco comprises the leaves of a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2; and producing said tobacco product from said cured tobacco.

In some embodiments, the invention provides a reduced-nicotinic alkaloid tobacco product produced from a *Nicotiana* plant or plant part of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2.

The present invention further provides a method of producing a blended tobacco, comprising: a) providing a first tobacco; b) providing a second tobacco, wherein the second tobacco is produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2; and c) blending said first tobacco with said second tobacco so as to produce said blended tobacco. In some embodiments, the first and the second tobacco may be produced from a *Nicotiana* plant of the invention, wherein, in some embodiments, the first tobacco and second tobacco are from different *Nicotiana* plant varieties both having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2.

In other aspects of the present invention, a method is provided for producing a blended reduced nicotine tobacco, the method comprising: a) providing a first tobacco; b) providing a second tobacco, wherein the second tobacco is produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2; and c) blending said first tobacco with said second tobacco so as to produce said blended reduced nicotine tobacco. In some embodiments, first and the second tobacco may be produced from a *Nicotiana* plant of the invention, wherein, in some embodiments, the first tobacco and second tobacco are from different *Nicotiana* plant varieties both having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2. As an example, both flue-cured and air-cured tobaccos are components of the common American blend cigarette. Thus, in some embodiments of the invention, a low nicotinic alkaloid tobacco product may be produced by blending a low nicotine burley variety with a high nicotine flue-cured variety, each variety having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2, thereby reducing the overall nicotinic alkaloid (e. g., nicotine, anatabine, nornicotine, anabasine, and the like) content of the low alkaloid tobacco product.

As is well known in the art, a tobacco formulation for a tobacco product can incorporate other components in addition to tobacco which can alter the bitterness, sweetness, sourness or saltiness of the formulation; enhance the perceived dryness or moistness of the formulation; or the degree of tobacco taste exhibited by the formulation. Such other components may be salts (e.g., sodium chloride, potassium chloride, sodium citrate, potassium citrate, sodium acetate, potassium acetate, and the like); natural sweeteners (e.g., fructose, sucrose, glucose, maltose, mannose, galactose, lactose, and the like); artificial sweeteners (e.g., sucralose, saccharin, aspartame, acesulfame K, and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like); binders (e.g., povidone, sodium carboxymethylcellulose and other modified cellulosic types of binders, sodium alginate, xanthan gum, starch-based binders, gum arabic, lecithin, and the like); pH adjusters or buffering agents (e.g., metal hydroxides, preferably alkali metal hydroxides such as sodium hydroxide and potassium hydroxide, and other alkali metal buffers such as potassium carbonate, sodium carbonate, sodium bicarbonate, and the like); colorants (e.g., dyes and pigments, including caramel coloring and titanium dioxide, and the like); humectants (e.g. glycerin, propylene glycol, and the like); preservatives (e.g., potassium sorbate, and the like); syrups (e.g., honey, high fructose corn syrup, and the like); disintegration aids (e.g., microcrystalline cellulose, croscarmellose sodium, crospovidone, sodium starch glycolate, pregelatinized corn starch, and the like); antioxidants (e.g., ascorbic acid, grape seed extracts and oils, polyphenol-containing materials such as green tea extract and black tea extract, peanut endocarb, potato peel, and the like (See Santhosh et al., *Phytomedicine*, 122:16-220 (2005); incorporated herein by reference); and flavoring agents. Flavoring agents may be natural or synthetic, and include, but are not limited to, fresh, sweet, herbal, confectionary, floral, fruity or spice. Specific types of flavors include, but are not limited to, vanilla, coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, grape, lemon, orange, apple, peach, lime, cherry, and strawberry. (See Leffingwill et al., *Tobacco Flavoring for Smoking Products*, R. J. Reynolds Tobacco Company (1972)). Flavorings also can include components that are considered moistening, cooling or smoothening agents, including, but not limited to, eucalyptus. These flavors may be provided alone or in a composite (e.g., spearmint and menthol, or orange and cinnamon). Representative types of components are also set forth in U.S. Pat. No. 5,387,416 to White et al. and PCT Application Publication No. WO 2005/041699 to Quinter et al., the relevant portions of each of which is incorporated herein by reference. Thus, in some embodiments, the tobacco product of the invention may comprise a flavoring component or a scent.

The amount of tobacco within the tobacco formulation may vary. In particular embodiments, the amount of tobacco within the tobacco formulation is at least about 25 percent to at least about 40 percent, on a dry weight basis (e.g., 25, 26, 27, 28, 29, 30, 31, 32, 33, 34, 35, 36, 37, 38, 39, 40% dry weight, and any value or range therein). The amounts of other components within the tobacco formulation preferably are in excess of about 25 percent to about 40 percent, on a dry weight basis.

In some embodiments of the present invention, methods are provided wherein the amount of nicotine in a human that uses tobacco is reduced, the method comprising providing to said human any of the tobacco products of the present invention.

In still other aspects of the present invention, a method is provided for reducing the nicotine consumption of a tobacco user, the method comprising: (a) providing said tobacco user a first tobacco product comprising tobacco produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2; and (b) providing said tobacco user a second tobacco product comprising tobacco produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2; wherein said second tobacco product comprises less nicotine than said first tobacco product.

In some aspects of the invention, a tobacco user can be provided with additional tobacco products comprising tobacco produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2; wherein said additional tobacco products comprise sequentially reduced amounts of nicotine, starting with a third product that comprises less nicotine than said first or second tobacco product.

In other embodiments of the present invention tobacco-use cessation kits are provided, wherein the tobacco-use cessation kits comprise a tobacco product selected from the tobacco products of any of the products of the present invention produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2.

In still other embodiments, the present invention provides a kit comprising a first tobacco product that comprises nicotine and a second tobacco product that comprises an amount of nicotine less than the amount in the first tobacco product, wherein said first or second tobacco product comprises a tobacco product produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2.

In yet other embodiments, the present invention provides a product produced from a *Nicotiana* plant of the invention having reduced nicotinic alkaloid content and comprising a mutation in (a) a BBLe polynucleotide having 97% identity to the nucleotide sequence of SEQ ID NO:3, (b) a BBLd-1 polynucleotide having 97% identity to the nucleotide sequence of SEQ ID NO:1, and/or (c) a BBLd-2 polynucleotide having 97% identity to the nucleotide sequence of SEQ ID NO:2, wherein the product produced is selected from the group consisting of industrial enzymes, pharmaceuticals, cosmetic components, human and livestock feeds, food additives, and fermentation products.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. BBL Mutations

To establish whether silencing the BBL gene family represents a viable means of obtaining reduced nicotine tobacco plants under conventional field growth conditions, we employed an RNAi approach (Lewis et al., 2015). Kajikawa et al., (2011) reported four unique BBL isoforms, designated BBLa, BBLb, BBLc and BBLd. To maximize the probability of suppressing the entire gene family, a 212 bp fragment from the most highly conserved region was selected. The anti-BBL RNAi construct was generated specifically against the BBLa sequence because an in silico analysis of the tobacco EST sequences represented in GenBank suggested that it was the most highly expressed of the BBL isoforms. The 212 bp fragment from BBLa was 94%, 93% and 84% identical to the analogous regions of BBLb, BBLc and BBLd, respectively. Although the anti-BBL RNAi construct shared the least sequence identify with BBLd, both the in silico EST analysis and a reverse transcriptase PCR analysis conducted by Kajikawa et al. (2011) suggested that the BBLd isoform is minimally expressed compared to the other isoforms.

Flue-cured tobacco cultivar 'K326' was transformed with the anti-BBL RNAi construct and ten independent 35S: BBL-RNAi DH lines were selected for evaluation in replicated field experiments for alkaloid profiles, yield, and cured leaf quality. Six of the ten tested RNAi lines exhibited nicotine levels in cured leaf that were significantly lower ($P<0.05$) than that observed for the untransformed control line, K326 (Table 1). The remaining four RNAi lines produced nicotine levels that were roughly equivalent to that of K326. This is likely because the RNAi mechanism was not functioning in these transgenic lines. Transgenic line DH32 exhibited the lowest percent nicotine in cured leaf (0.414%), while untransformed K326 produced 2.454% nicotine. The lowest nicotine level (0.299%) was produced by LAFC53, a nic1/nic1 nic2/nic2 isoline of flue-cured tobacco cultivar NC95.

TABLE 1

Means for measured characteristics for transgenic RNAi doubled haploid lines and associated checks.

| Genotype | Cured Leaf | | | | | | | | | | |
|---|---|---|---|---|---|---|---|---|---|---|---|
| | % Nicotine | % Nornicotine | % Anabasine | % Anatabine | % DMN | % Total Alkaloids | % Reducing Sugars | Yield (kg $ha^{-1}$) | Cwt Value ($ $cwt^{-1}$) | Cash Return ($ $ha^{-1}$) | Grade Index |
| K326 Nbl-RNAi DH22A | 0.5362 | 0.0784 | 0.0124 | 0.0143 | 0.0152 | 0.6565 | 13.71 | 1685 | 315.43 | 6439.64 | 83.3 |
| K326 Nbl-RNAi DH32 | 0.4136 | 0.0890 | 0.0132 | 0.0073 | 0.0209 | 0.5440 | 12.67 | 1628 | 316.78 | 6551.81 | 83.7 |
| K326 Nbl-RNAi DH16A | 0.4720 | 0.0789 | 0.0125 | 0.0079 | 0.0163 | 0.5876 | 13.79 | 1439 | 309.34 | 4774.54 | 80.1 |
| K326 Nbl-RNAi DH19 | 1.0442 | 0.0864 | 0.0178 | 0.0358 | 0.0165 | 1.2007 | 12.91 | 1615 | 322.99 | 5800.20 | 85.5 |
| K326 Nbl-RNAi DH303 | 0.9110 | 0.0859 | 0.0166 | 0.0233 | 0.0178 | 1.0547 | 14.08 | 1944 | 311.13 | 7166.99 | 83.3 |
| K326 Nbl-RNAi DH16B | 0.7288 | 0.0781 | 0.0147 | 0.0283 | 0.0159 | 0.8658 | 13.32 | 1591 | 317.49 | 5831.29 | 84.0 |
| K326 | 2.4541 | 0.0559 | 0.0206 | 0.1188 | 0.0104 | 2.6598 | 14.71 | 2343 | 317.29 | 8254.99 | 83.9 |

TABLE 1-continued

Means for measured characteristics for transgenic RNAi doubled haploid lines and associated checks.

| | Cured Leaf | | | | | | | | | | |
|---|---|---|---|---|---|---|---|---|---|---|---|
| Genotype | % Nicotine | % Nornicotine | % Anabasine | % Anatabine | % DMN | % Total Alkaloids | % Reducing Sugars | Yield (kg ha$^{-1}$) | Cwt Value ($ cwt$^{-1}$) | Cash Return ($ ha$^{-1}$) | Grade Index |
| NC95 | 2.8870 | 0.0636 | 0.0303 | 0.2217 | 0.0099 | 3.2125 | 12.95 | 1722 | 306.66 | 6105.61 | 81.3 |
| LAFC53 | 0.2990 | 0.0128 | 0.0035 | 0.0201 | 0.0074 | 0.3428 | 8.55 | 1844 | 303.98 | 6519.67 | 79.4 |
| LSD (0.05) | 0.3998 | 0.0160 | 0.0032 | 0.0216 | 0.0039 | 0.4067 | 3.59 | 304 | 25.64 | 1098.66 | 6.4 |

% total alkaloids was calculated as: % total alkaloids = (% nicotine + % nornicotine + % anatabine + % anabasine + % DMN).

All six of the RNAi lines with significantly lower percent nicotine relative to K326 also exhibited significantly ($P<0.05$) lower anatabine and total alkaloid levels (Table 1) in the cured leaf. Five of these six lines also exhibited significantly ($P<0.05$) lower levels of anabasine. All six were higher for percent nornicotine and percent dihydrometanicotine (DMN), although these numerical differences were very small. The six RNAi lines exhibiting significantly lower nicotine and total alkaloid levels relative to K326 produced significantly lower ($P<0.05$) cured leaf yields as compared to untransformed K326, with an average difference of 693 kg ha$^{-1}$ (Table 1). No significant differences were detected, however, between K326 and any of the RNAi lines for cured leaf quality as measured by percent reducing sugars, value per hundredweight ($ cwt$^{-1}$), or grade index. In contrast, the LAFC53 plants homozygous for nic1 and nic2 were clearly of lower quality, based on their overall lower grade index and reducing sugar content. Much of the quality reduction observed with LAFC53 was likely due to a delayed ripening phenotype associated with this line when grown in the field. Overall, the results of this experiment demonstrate that inhibition of BBL gene expression can give rise to tobacco plants with significantly reduced nicotine while retaining important quality characteristics (Lewis et al., 2015).

Although RNAi suppression of BBL gene activity was effective in producing high quality, reduced nicotine lines, there are many obstacles associated with the commercialization of a transgenic crop, such as the enormous costs and lengthy timelines associated with the deregulatory process, as well as the fear of rejection by consumers who are philosophically opposed to genetically modified (GM) crops. To provide a non-GM alternative, we screened an ethyl methane sulfonate (EMS)-mutagenized population of burley tobacco breeding line DH98 325-6 for mutations in BBLa, BBLb and BBLc, the three most actively transcribed genes of the BBL gene family. We did not screen for mutations in BBLd because, as described above, this isoform appears to be minimally expressed in comparison to the other three. After conducting thousands of high-throughput PCR and DNA sequencing reactions on this population, we were successful in identifying knockout (truncation) mutations in each of the three BBL genes that were screened for (Lopez, 2011; Lewis et al., 2015).

Sexual crossing in accompaniment with SNP genotyping was used to combine the identified truncation mutations in BBLa, BBLb, and BBLc in all possible homozygous combinations in the mutagenized DH98-325-6 genetic background. Alkaloid profiles were compared among plants of all seven possible bbl mutant genotypic classes as well as wild-type (WT) segregants grown in a single field environment (Table 2). Wide numerical ranges were observed among the genotypic classes for percent nicotine, nornicotine, anatabine, and total alkaloids. Nornicotine was the most prevalent alkaloid in all of these genotypes because DH98-325-6 has a high genetic potential to convert nicotine to nornicotine due to an active nicotine demethylase gene designated as CYP82E4 (Lewis et al., 2010). Genotypes homozygous for single mutations exhibited slight to intermediate reductions in total alkaloids. Of the three single mutation genotypes, the bbla/bbla mutation was found to have the largest numerical effect, while the bblb/bblb mutation was found to have the second largest effect. The bblc/bblc mutation, by itself, provided only a small reduction in percent total alkaloids. The double mutant combination bbla/bbla bblb/bblb BBLc/BBLc and the triple homozygous mutation combination bbla/bbla bblb/bblb bblc/bblc exhibited the second lowest and lowest levels of total alkaloid accumulation, respectively. These levels were substantially and significantly lower than that for WT DH98-325-6 segregants (Table 2). Although nornicotine was the major alkaloid in these particular materials, once these mutations are transferred to a normal, non-converter tobacco line, similar results are expected with the exception that nicotine would represent the predominant alkaloid species rather than nornicotine. These results confirm that inactivation of BBL gene function represents an effective means of producing low alkaloid tobacco plants, and that this can be accomplished using a non-GM strategy (Lewis et al., 2015).

TABLE 2

Alkaloid content (% dry weight) of DH98 325-6 burley plants possessing various combinations of BBL EMS-induced knockout mutations.

| | Genotype Means | | | | |
|---|---|---|---|---|---|
| Genotype | Nic | Nor | Anab | Anat | TA |
| NS BBLa/BBLb/BBLc | 0.0907 | 1.4121 | 0.0109 | 0.0984 | 1.6121 |
| SM BBLa/BBLb/bblc | 0.1116 | 1.3256 | 0.0109 | 0.1136 | 1.5617 |
| SM BBLa/bblb/BBLc | 0.0885 | 0.9555 | 0.0090 | 0.0817 | 1.1347 |
| SM bbla/BBLb/BBLc | 0.1086 | 0.9428 | 0.0111 | 0.0583 | 1.1208 |
| DM BBLa/bblb/bblc | 0.0471 | 1.1847 | 0.0119 | 0.1042 | 1.3478 |
| DM bbla/BBLb/bblc | 0.1054 | 1.1470 | 0.0139 | 0.0916 | 1.3579 |
| DM bbla/bblb/BBLc | 0.0056 | 0.3309 | 0.0126 | 0.0073 | 0.3564 |
| TM bbla/bblb/bblc | 0.0050 | 0.1001 | 0.0080 | 0.0058 | 0.1188 |

NS, null segregants (wild type);
SM, single gene mutants;
DM, double mutants;
TM, triple mutants;
TA, total alkaloid.

Example 2. Identification of New Members of the BBL Gene Family

Kajikawa et al. (2011) described the BBL gene family of tobacco as being comprised of four members, which they designated BBLa, BBLb, BBLc and BBLd. We conducted a BLAST-based analysis of the various databases found in GenBank to determine whether there was evidence for the existence of any other BBL family members within the tobacco genome. These results revealed the presence of two additional BBL family members. One of these shares 95% nucleotide identity and 94% predicted amino acid identity with BBLd. Given that BBLd and this new isoform are very closely related to each other and are quite distinct from the other BBL genes (sharing less than 80% identity with any other gene family member), we refer to these sequences as BBLd-1 (the original BBLd reported by Kajikawa et al., 2011) and BBLd-2 (the new isoform). The other novel BBL family member that we identified shares 90-92% nucleotide identity with the previously characterized BBLa, BBLb and BBLc sequences. We designate this new family member BBLe. The DNA and predicted protein sequences of BBLe, BBLd-1 and BBLd-2 are shown below. Start and stop codons are in bold, underlined type. Locations of the 22 bp target sites of the custom-designed meganuclease enzymes are highlighted grey.

```
BBLd-1 (same as GenBank accession #AB604221)
                                                    SEQ ID NO: 1
ATGAAACGAAATATATCCATGTTTCTTCAGCTTCTGCTCATTATTCTGATGATGATCAGCTT

CTTATTTACTTCTCTTCTTGTACCTTCGGTCTCTGCAACAACTCTCAATACCATTTCCACCT

GTTTAATCAATTACAAAGTCAGTAACTTCTCTGTTTACCCAACAAGGAATCATGCTGGTAAT

AGTTACTATAACTTGCTTGATTTCTCCATTCAGAATCTCCGATTCGCAGCGTGCTCTAAACC

AAAACCAACTGTCATTATCGTACCAGAGAGCAAGGAGCAGCTGGTGAGCAGCGTTCTGTGTT

GCAGACAAGGCTCGTATGAAATCAGAGTAAGGTGCGGTGGACACAGTTATGAAGGGACTTCA

TCAGTTTCCTTTGATGGTTCCCCATTTGTGGTCATTGATTTGATGAAATTAGACGGCGTTTC

AGTGGATGTGGATTCAGAAACCGCGTGGGTACAGGGCGGCGCTACACTTGGCCAGACTTATT

ATGCCATTTCCCGAGCCAGCAACGTTCATGGATTTTCAGCTGGTTCTTGCCCAACAGTTGGG

GTTGGCGGGCACATTTCCGGGGGTGGTTACGGATTTTTATCCAGAAAATATGGACTTGCTGC

TGATAACGTGGTGGATGCTCTTCTTGTTGATGCGGAAGGACGGCTATTAGACCGCAAAGCCA

TGGGAGAAGAAATCTTTTGGGCCATCAGAGGTGGAGGTGGAGGAATTTGGGGAATCATTTAC

GCCTGGAAAATCCGATTGCTCAAAGTGCCCAAGACCGTGACCAGTTTCATAATCCCTAGGCC

TGGCTCCAAACGATATGTGTCCCAACTAGTTCACAAATGGCAACTTGTTGCACCAAAGTTAG

AGGATGAATTTTATCTATCGATCTCCATGAGCTCTCCTAGTAAAGGAAACATTCCTATTGAA

ATAAATGCCCAATTCAGCGGATTTTACCTAGGTACAAAAACCGAAGCCATTTCCATCTTGAA

TGAGGCCTTTTCGGAGTTGGGAGTTCTGGAAGGTGACTGCAAAGAAATGAGTTGGATTGAAT

CAACACTTTTCTTCTCCGAATTAAATGACGTTGCGAATTCCTCCGATGTCTCTCGTTTGAAA

GAGCGTTACTTTGAAAACAAATCATACTTCAAAGCCAAATCAGACTATGTGAAGACCCCAAT

TTCAGTGGGTGGGATTATGACGGCTCTTAATGTTCTTGAGAAAGAACCCAACGGACATGTCA

TCTTGGACCCTTATGGTGGAGCCATGCAAAGAATTAGTGAGGAAGCTATTGCTTTCCCTCAT

AGAAAGGGTAACCTTTTCGGAATTCAATATCTAGTAGTGTGGAAAGAAAAGGACAATAATAA

TATTGTCAAGAGCAATATTGGGTACATAGAGTGGATAAGAGAGTTTTACAATACAATGGCAC

CCCATGTTTCAAGTTCACCTAGGGCAGCTTATGTCAACTACATGGATCTGGACCTTGGAGTG

ATGGACGACTACTTATTGCCATGTACTAGTACTACTGCGTCTGCTAATCATGCCGTGGAGAG

AGCAAGGGTCTGGGGTGAAAAGTATTTCTTGAATAACTATGATAGATTGGTCAAAGCTAAGA

CAAAAATTGACCCACTAAACGTTTTCGACATCAACAGGGCATCCCTCCTTTGTTCGCCTCA

ATGCAAGAGTATACCTATAGTAGTAAATGA

Predicted amino acid sequence
                                                    SEQ ID NO: 4
MKRNISMFLQLLLIILMMISFLFTSLLVPSVSATTLNTISTCLINYKVSNFSVYPTRNHAGN

SYYNLLDFSIQNLRFAACSKPKPTVIIVPESKEQLVSSVLCCRQGSYEIRVRCGGHSYEGTS

SVSFDGSPFVVIDLMKLDGVSVDVDSETAWVQGGATLGQTYYAISRASNVHGFSAGSCPTVG

VGGHISGGGYGFLSRKYGLAADNVVDALLVDAEGRLLDRKAMGEEIFWAIRGGGGGIWGIIY
```

```
AWKIRLLKVPKTVTSFIIPRPGSKRYVSQLVHKWQLVAPKLEDEFYLSISMSSPSKGNIPIE

INAQFSGFYLGTKTEAISILNEAFSELGVLEGDCKEMSWIESTLFFSELDDVANSSDVSRLK

ERYFENKSYFKAKSDYVKTPISVGGIMTALNVLEKEPNGHVILDPYGGAMQRISEEAIAFPH

RKGNLFGIQYLVVWKEKDNNNIVKSNIGYIEWIREFYNTMAPHVSSSPRAAYVNYMDLDLGV

MDDYLLPCTSTTASANHAVERARVWGEKYFLNNYDRLVKAKTKIDPLNVFRHQQGIPPLFAS

MQEYTYSSK
```

BBLd-2

SEQ ID NO: 2

```
ATGAAACGAAATATATCCATGTCTCTTCAGCGTTTGCTCATAATTCTGATGATGATCAGCTT

CTTATTTACTTCTCTTCTTGTACCTTCCGTCTCTGCTACAAATCTCAATACCATTTCCACCT

GTTTGATCAATTACAAAGTCAGTAACTTCTCTGTTTATCCAACAAGGAATCATGCTGGTAAT

AGGTACTATAACTTGCTTGATTTCTCCATTCAGAATCTCCGATTCGCAGCGTCCTCTAAACC

AAAACCAACGGTCATTATCGTACCAGAGAGCAAGGAGCAGCTGGTGAGCAGCGTTCTGTGTT

GCAGACAAGGTTCTTATGAAATCAGAGTAAGGTGCGGAGGACACAGTTATGAAGGGACTTCT

TACGTTTCCTTTGATGGTTCCCCATTTGTGGTCATTGATTTGATGAAATTAGATGATGTTTC

GGTAGATTTGGATTCCGAAACCGCGTGGGTACAAGGTGGCGCTACACTTGGCCAGACTTATT

ATGCCATTTCCCGGGCCAGTGACGTTCATGGATTTTCAGCTGGTTCTTGCCCAACAGTTGGG

GTTGGGGGCCACATTTCCGGGGGTGGCTTTGGATTTTTATCAAGAAAATATGGACTTGCTGC

TGATAACGTGGTGGATGCTCTTCTTGTTGATGCGGAAGGACGGCTATTAGACCGCAAAGCCA

TGGGAGAAGAAGTGTTTTGGGCCATCAGAGGTGGTGGTGGAGGAATTTGGGGAATCATTTAC

GCCTGGAAAATCCGATTGCTCAAAGTGCCCAAGACTGTGACTAGTTTCATAGTCCCTAGGCC

TGGCTCCAAACGATATGTGTCCCAACTAGTTCACAAATGGCAACTTGTTGCACCAAAGTTAG

ACGATGACTTTTATCTATCGATCTCCATGAGCTCTGCTAGTAAAGGAAACATTCCTATTGAA

ATAAATGCCCAATTCAGCGGATTTTACCTAGGTACAAAAACCGAAGCCATTTCCATCTTGAA

TGAGGCCTTTCCGGAGTTGGGAGTTGTGGAAAGTGACTGCAAAGAAATGAGTTGGATTGAAT

CAACACTTTTCTTCTCCGAATTAGATAACGTTGCGAACACCTCCGATGTCTCTCGTTTGAAA

GAGCGTTACTTTGAAAACAAATCATACTTCAAAGCCAAATCAGACCATGTGAAGACCCCAAT

TTCAGTGGGAGGGATTATGACAGCTCTTGATGTTCTTGAGAAAGAACCAAATGGACATGTCA

TCTTTGACCCTTATGGTGCAGCCATGCAGAGAATTAGCGAGGAAGCTATTGCTTTCCCTCAT

AGAAAGGGTAACCTATTCAGAATTCAATATCTAGTAGTGTGGAAAGAAAAGGACAATAATAA

TATTGCCAAGAGCAATGGGTACATAGAGTGGATAAGAGAGTTTTACAATACAATGGCACCCC

ATGTTTCTAGTTCACCTAGGGCAGCTTATGTCAACTATATGGATCTGGACCTTGGAGTGATG

GACGACTACTTAATGCTAAATACTAGTATTACTGCCTCTGCTGATCATGCCGTGGAGAGAGC

AAGGGTCTGGGGTGAAAAGTATTTCTTGAATAACTATGATAGATTGGTCAAAGCTAAGACAA

AAATTGACCCACTAAACGTTTTTCGACATCAACAGGGCATCCCTCCTATGTTCGCCTCAATG

CCAGAGCATACCTATAGTAGTAAATGA
```

Predicted amino acid sequence

SEQ ID NO: 5

```
MKRNISMSLQRLLIILMMISFLFTSLLVPSVSATNLNTISTCLINYKVSNFSVYPTRNHAGN

RYYNLLDFSIQNLRFAASSKPKPTVIIVPESKEQLVSSVLCCRQGSYEIRVRCGGHSYEGTS

YVSFDGSPFVVIDLMKLDDVSVDLDSETAWVQGGATLGQTYYAISRASDVHGFSAGSCPTVG

VGGHISGGGFGFLSRKYGLAADNVVDALLVDAEGRLLDRKAMGEEVFWAIRGGGGGIWGIIY
```

-continued

AWKIRLLKVPKTVTSFIVPRPGSKRYVSQLVHKWQLVAPKLDDDFYLSISMSSASKGNIPIE

INAQFSGFYLGTKTEAISILNEAFPELGVVESDCKEMSWIESTLFFSELDNVANTSDVSRLK

ERYFENKSYFKAKSDHVKTPISVGGIMTALDVLEKEPNGHVIFDPYGAAMQRISEEAIAFPH

RKGNLFRIQYLVVWKEKDNNNIAKSNGYIEWIREFYNTMAPHVSSSPRAAYVNYMDLDLGVM

DDYLMLNTSITASADHAVERARVWGEKYFLNNYDRLVKAKTKIDPLNVFRHQQGIPPMFASM

PEHTYSSK

BBLe

SEQ ID NO: 3

ATGTTTCCAATCATAATTCTGATCAGCTTTTCATTTACTTTCCTCTTTGCTAGTGTTACTAG

TGGAGCAGGAGGAGTTACAAATCTTTCCACCTGTTTAATCAACCACAATGTCCATAACTTCT

CTATTTACCCCACAAAGAATGATCAAAGTAGTAGTAATTACTTTAACTTGCTCGATTTTTCC

CTTCAGAATCTTCGATTTGCTGCATCTTACATGCCGAAACCAACGGTCATTATCCTACCAAA

CAGCAAAGAGGAGCTCGTGAGTACCATTCTTTGTTGCAGACAAACATCTTATGAAATCAGAG

TAAGGTGCGGAGGACACAGTTACGAGGGAACTTCTTACGTTTCCTTTGACGGTTCCCCTTTC

GTGATCGTTGACTTGATGAAATTAGACGACGTTTCAGTAGATTTGGATTCCGAAACAGCTTG

GGCTCAGGGCGGCGCAACAATTGGCCAAATTTATTACGCCATTTCCAGGGTTAGTGACGTTC

ATGCATTTTCAGCAGGTTCGGGACCAACAGTAGGATCTGGAGGTCATATTTCAGGTGGCGGC

TTTGGACTAATGTCCAGAAAATTCGGACTCGCTGCTGATAGTGTCGTTGATGCTCTTCTAAT

TGATGCTGAAGGACGGTTATTAGACCGGAAAGCCATGGGAGAAGACGTATTTTGGGCAATCA

GAGGTGGCGGCGGTGGAAATTGGGGAATTATTTATGCCTGGAAAATTCGATTACTCAAAGTG

CCTAAAATCGTAACAACTTGTATGATCTATAGGCCTGGATCCAAACAATACGTGGCTCAACT

ACTTCAGAAATGGCAAATAGTTACTCCAAATTTGGCCGATGATTTTACTCTAGGAGTACTCA

TGAGACCTATAGATCTGCGGGCGGATATGAATTACGGAAATACTACTCCTATTGAAACATTT

CCCCAATTCAATGCACTTTATTTGGGTCCAAAAACTGAAGCGGTTTCCATATTAAATGAGGC

ATTTCCAGAGCTGGACGCTAAGAATGATGACGCCAAAGAAATGACTTGGATTGAGTCAGCAC

TTTTCTTTTCCGAATTAGATAACGTATTCGGGAACTCCTCTGACGATATCTCCCGTTTGAAA

GAACGCTACATGGACGCAAAAACTTTCTTCAAAGGCAAATCAGATTTTGTGAAGACTCCATT

TTCAATGGACGCGATGATGACAGCTCTTGTTGAACTCGAGAAAAACCCCAAGTCATTCCTTG

TCTTCGATCCTTATGGCGGAGTCATGGACAAGATTAGTGATCAAGCTATTGCTTTCCCTCAT

CGAAAGGGTAACCTTTTCGCGGTTCAATATTATGCATTTTGGAACGAAGAGGACGATGCCAA

GAGCAACGAGTACATAGAGTGGACAAGGGGATTTTACAATAAAATGGCGCCTTTTGTTTCAA

GCTCGCCAAGGGGAGCTTATATCAACTACTTGGATATGGATCTTGGAGTGAATATGGACGAC

GACTACTTACTGCGAAATGCTAGTAGTCGTAGTTCTTCTTCCTCTGTTGATGCTGTGGAGAG

AGCTAGAGCGTGGGGTGAAATGTATTTCTTGCATAACTATGATAGGTTGGTTAAAGCTAAGA

CACAAATTGATCCACTAAATGTTTTTCGACATGAACAGAGTATACCTCCTATGCTTGGTTCA

ACGCAAGAGCACAGTAGTGAATGA

Predicted amino acid sequence

SEQ ID NO: 6

MFPIIILISFSFTFLFASVTSGAGGVTNLSTCLINHNVHNFSIYPTKNDQSSSNYFNLLDFS

LQNLRFAASYMPKPTVIILPNSKEELVSTILCCRQTSYEIRVCGGHSYEGTSYVSFDGSPF

VIVDLMKLDDVSVDLDSETAWAQGGATIGQIYYAISRVSDVHAFSAGSGPTVGSGGHISGGG

FGLMSRKFGLAADSVVDALLIDAEGRLLDRKAMGEDVFWAIRGGGGGNWGIIYAWKIRLLKV

PKIVTTCMIYRPGSKQYVAQLLQKWQIVTPNLADDFTLGVLMRPIDLRADMNYGNTTPIETF

-continued

```
PQFNALYLGPKTEAVSILNEAFPELDAKNDDAKEMTWIESALFFSELDNVFGNSSDDISRLK

ERYMDAKTFFKGKSDFVKTPFSMDAMMTALVELEKNPKSFLVFDPYGGVMDKISDQAIAFPH

RKGNLFAVQYYAFWNEEDDAKSNEYIEWTRGFYNKMAPFVSSSPRGAYINYLDMDLGVNMDD

DYLLRNASSRSSSSSVDAVERARAWGEMYFLHNYDRLVKAKTQIDPLNVFRHEQSIPPMLGS

TQEHSSE
```

In silico analyses of EST databases can serve as a useful indicator to predict the relative contribution of individual members of a gene family toward the overall transcript pool. The results of our in silico analysis of the BBL family is shown below in Table 3.

TABLE 3

In silico analysis of BBL gene expression.

| BBL Isoform | EST Library Hits | Root-Specific ESTs[a] |
|---|---|---|
| BBLa | 38 | 38 |
| BBLb | 11 | 10 |
| BBLc | 16 | 16 |
| BBLd-1 | 2 | 1 |
| BBLe | 4 | 4 |

[a] In addition to cDNA from libraries generated solely from root tissue, cDNAs isolated from pooled leaf, flower, and root cDNA libraries were also included.

Consistent with the characterization of the BBL gene family reported by Kajikawa et al. (2011), the in silico analysis suggests that BBLa, BBLb and BBLc are the most highly transcribed members of this gene family. This is also consistent with the dramatic reduction in alkaloid content observed in tobacco plants mutated at these three loci (Table 2). Although fewer ESTs were found corresponding to BBLd-1 and BBLe, their presence in the EST database proves that they are in fact transcribed and are therefore likely to be contributing toward the overall BBL activity of the tobacco plant. This is particularly true for BBLe given its greater sequence similarity to BBLa, BBLb and BBLc, as well as its increased representation in the in silico analysis compared to BBLd-1. Although no ESTs were found that corresponded to BBLd-2, we cannot rule out the possibility that this isoform is also transcribed at a low level and thereby contributes toward overall cellular BBL activity.

The work described in Example 1 and that reported in Lewis et al. (2015) demonstrate that it is possible to produce low alkaloid tobacco plants that maintain favorable quality properties by inhibiting the function of genes of the BBL family. Despite the substantial progress that has been made in this area, the existing technology still falls short of what would be optimal for many low nicotine tobacco applications. The primary deficiency is that the alkaloid levels remaining in the current art are still not as low as would be desired for certain applications. For example, the cured leaf of the RNAi line displaying the greatest reduction in nicotine content in Table 1 (DH32) still possessed about 17% of the nicotine observed in the normal K326 plants. For the EMS-mutagenized DH98 325-6 materials, the triple mutant bbl plants retained about 7.5% of the total alkaloid content observed in the null segregant controls. There remains a need to develop tobacco cultivars that produce and accumulate even lesser quantities of nicotine within high quality tobacco backgrounds than has been previously described, or is even possible using the existing art.

Example 3. Targeted Mutagenesis of BBL Genes

Another deficiency in the current technology has been the reliance on non-target-specific mutagens such as EMS in order to generate gene mutations in plants for situations where it is preferable that the end product be non-transgenic. Mutagens like EMS function to randomly distribute mutations throughout the entire genome. In order to obtain a reasonable likelihood of finding a mutation in a gene of interest using nontarget-specific agents, one must treat the plant in a manner whereby mutations are incorporated at a high density throughout the entire genome. Once a mutation in a gene of interest is identified in a plant from such a mutagenized population, extensive backcrossing is then required to attempt to eliminate all the undesirable mutations distributed throughout the genome that will be found in that plant as well. Should an undesirable secondary mutation be closely linked to the mutation of interest, it can become difficult to separate it from the desired mutant trait. A problem frequently encountered using random mutation breeding approaches is that the linked deleterious secondary mutations prevents incorporation of the mutant trait of interest into high quality commercial cultivars in a manner that does not negatively affect important agronomic and/or quality traits. With the recent advent of molecular biology-based precision mutagenesis technologies, it is now possible to induce mutations into a specific gene or genes of interest without introducing unwanted random mutations throughout the genome. These technologies promise to greatly increase the ability to introduce specific desired mutations within the genome of a crop of interest in a manner than do not otherwise negatively impact favorable attributes of the recipient parent, as well as reduce or eliminate the time involved with conducting extensive backcrossing, as is currently required for traditional mutation breeding approaches.

To date there have been four distinct classes of designer nucleases that have been developed for the purpose of targeted gene modification in eukaryotes: (1) zinc finger nucleases (ZFNs); (2) custom-designed homing enzymes, or "meganucleases"; (3) transcription activator-like effector nucleases (TALENs); and (4) clustered, regularly interspaced, short palindromic repeats (CRISPR)-associated (Cas) nucleases (Puchta and Fauser, 2014). When introduced into a plant cell, a custom-designed nuclease will bind to its target site(s) and create a double-stranded break in the DNA at that location (Curtin et al., 2012; Puchta and Fauser, 2014). Plants have two distinct cellular repair mechanisms that function in response to DNA breaks: non-homologous end joining (NHEJ) and homologous recombination (HR). The NHEJ repair system functions by religating the broken ends, whereas the HR-mediated system utilizes a homologous sequence as a donor template to repair the break via recombination. In most plant cells, the NHEJ system predominates. Because NHEJ is error-prone, however, the repeated cutting of a target site by a nuclease and religation by NHEJ will lead to a high frequency of short deletions and/or short insertions at the cut site. When a nuclease targets an exon region of a gene, these in-dels frequently result in frame-shift mutations that effectively cause a loss of gene function. Thus the introduction of a custom-designed nuclease into a plant cell can serve as a powerful tool for knocking out the function of a targeted gene. Because the introduced transgene carrying the designer nuclease will nearly always integrate at a site that is unlinked to the gene(s) being targeted, it can be segregated away in subsequent generations of self-fertilization and/or crossing, resulting in plants in which the targeted endogenous gene(s) have been inactivated, but no longer carry any foreign DNA.

1. Development of Ultra-Low Nicotine Tobacco Cultivars by Targeted Mutagenesis of bbl Family Members Using Custom-Designed Nucleases A. Constructs Encoding Meganucleases Targeting BBLe, BBLd-1 and BBLd-2

Plasmids encoding meganucleases designed to cleave specific targets in the BBLe, BBLd-1 and BBLd-2 genes were produced by the company Precision Biosciences (Table 4). Construct BBL 1-2x.81 encodes a nuclease that was engineered to recognize a unique 22 bp sequence within BBLe. Due to the high sequence identity shared between BBLd-1 and BBLd-2, it was possible to design a single nuclease (BBL 7-8x.90) capable of targeting both of these genes. For each custom-designed nuclease, a 22 bp target site was chosen that failed to be present anywhere within the recently published *Nicotiana tabacum* reference genomes except for the intended gene targets (Sierro et al., 2014). The selection of unique target sites should help minimize the possibility of off-target cleavage elsewhere in the genome. Further core, the selected target sites occur in the upper one third of the gene sequences (see sequences in Example 2 above), upstream of the sequences encoding the highly conserved FAD binding domain Therefore mutation events leading to a frame shift at these locations would be predicted to produce completely nonfunctional protein products. Constructs BBL 1-2x.81 and BBL 7-8x.90 were cloned into the plant expression vector pCAMBIA2300 (cambia.org). Within pCAMBIA2300, transcription of the designer nucleases is driven by an enhanced 35S Cauliflower Mosaic Virus promoter, and selection is mediated via the nptII gene that confers resistance to the antibiotic kanamycin.

TABLE 4

Custom-designed nuclease constructs that target BBL genes.

| Target Gene | Target Site | Designer Nuclease |
| --- | --- | --- |
| BBLe | GAGGAGCTCGTGAGTACCATTC (SEQ ID NO: 7) | BBL 1-2x.81 |
| BBLd-1, BBLd-2 | GTCATTATCGTACCAGAGAGCA (SEQ ID NO: 8) | BBL 7-8x.90 |

B. Targeted Mutagenesis of BBLe, BBLd-1 and BBLd-2 Within a Triple Mutant bbla, bblb and bblc Background To determine whether introducing mutations in the BBLe, BBLd-1 and/or BBLd-2 genes can reduce nicotine levels below that which is attainable in plants homozygous for knockout mutations in the three previously characterized BBL genes (BBLa, BBLb and BBLc), constructs BBL 1-2x.81 and BBL 7-8x.90 were introduced into line TN90 (bbla/bblb/bblc) using standard *Agrobacterium*-mediated transformation protocols (Horsch et al., 1985). TN90 (bbla/bblb/bblc) was produced by backcrossing an original triple mutant bbla/bblb/bblc individual in its EMS-mutagenized DH98 325-6 background (Lewis et al., 2015) into the commercial burley cultivar TN90. Seven generations of backcrossing were conducted to bring the TN90 recurrent parent back to type and to vastly reduce the number of genome-wide EMS mutations present in the starting DH98 325-6 (bbla/bblb/bblc) materials. With each backcross generation, SNP markers specific for the debilitating bbla, bblb and bblc mutations were used to identify progeny carrying the desired bbl loci; upon completion of seven backcross generations, $BC_7F_2$ individuals were screened with the same markers to identify line TN90 (bbla/bblb/bblc) that is homozygous for all three bbl mutations.

Over 150 kanamycin resistant $T_0$ plants were screened for mutations in BBLe, BBLd-1 or BBLd-2. Mutation screening was conducted by isolating genomic DNA from the leaves of very young $T_0$ plants and amplifying the regions of interest through PCR using primers flanking the targeted cut sites. The resulting PCR products were subsequently analyzed by DNA sequence analysis. If a genome editing event occurred soon after transformation and prior to the first cell division, this can be readily detected on a sequence chromatogram as these sequences will diverge from wild type (WT) at the edited site. If there are two distinct sequencing patterns of equal intensity at the site of sequence divergence, one WT and the other edited, we classify this plant as being "monoallelic", as only one of the two alleles of the target gene would appear to have been mutated. Plants possessing a single edited sequence pattern, or two overlapping patterns that both differ from WT are designated "biallelic" events. Given the large number of cells that comprise a young tobacco leaf, editing events that occurred at a late-stage post-transformation and are only present in a small number of cells would not be detected using this screening method. Plants containing late event mutations would be considered "chimeric" and are of lesser interest as these editing events would be much less likely to be present in the germline and inherited by the progeny.

$T_0$ plants containing genome editing events mediated by constructs BBL1-2x.81 or BBL7-8x.90 are shown in FIG. 1. Nuclease-mediated editing is manifest as short deletions and/or insertions emanating from the predicted cut site of the enzyme. Of the eight $T_0$ plants identified with mutations in BBLe, seven were monoallelic for the mutation and one was biallelic (plant #143). Eight $T_0$ plants were also identified that displayed nuclease-induced mutations in BBLd-1, all of which were predicted to be monoallelic. For BBLd-2, nine monoallelic events and one biallelic event (plant #36) were observed amongst the $T_0$ plants screened. Two plants transformed with the BBL7-8x.90 construct possessed mutations in both BBLd-1 and BBLd-2 (#36 and #100). Overall, approximately 18% of the $T_0$ plants transformed with BBL1-2x.81 or BBL7-8x.90 screened positive for mutations at the intended BBL loci. This level of mutation efficiency is similar to that reported by others who have used custom-designed meganuclease enzymes for targeted mutagenesis in plants (Gao et al., 2010; Dewey and Lewis, 2014). Of particular interest are plants harboring deletion/insertion mutations in a BBLe, BBLd-1 and BBLd-2 gene whose net loss or gain of nucleotides is a number that is not divisible by three. Mutations of this nature would be predicted to lead to a completely nonfunctional protein product, as the reading frame of the gene sequences upstream of the mutation site would not be in frame with those downstream of the mutation. $T_0$ events that fit this description are underlined in FIG. 1.

2. Evaluation of Plants with BBLe, BBLd-1 and BBLd-2 Mutations

T$_0$ transgenics containing targeted mutations of interest are crossed and/or self-fertilized to produce progeny homozygous for the various possible mutant combinations and that have also segregated away the mutagenic transgene(s). Plants that lack any foreign DNA and carry various combinations of bbld-1, bbld-2 and bble mutations (all still within a triple mutant bbla/bblb/bblc background) are grown and cured according to standard industry practice and assayed for alkaloid content. Comparisons are made to the relevant original wild type genotype (e.g. TN90), as well as its relevant parental genotype homozygous for only the bbla, bblb and bblc mutant loci (e.g. TN90 (bbla/bblb/bblc)). In addition, all plants are evaluated for grade index and percent reducing sugars. The outcome is the development of high quality tobacco cultivars in commercially viable backgrounds that accumulate significantly less nicotine than their respective parental plants (bblabbla/bblbbblb/bblcbblc) due to the introduction and pyramiding of knockout mutations in the BBLe and/or BBLd-1 and/or BBLd-2 loci.

The foregoing is illustrative of the invention, and is not to be construed as limiting thereof. The invention is defined by the following claims, with equivalents of the claims to be included therein.

REFERENCES

Benowitz, N. L., Hall, S. M., Stewart, S., Wilson, W., Dempsey, D., and Jacob, P. (2007) Nicotine and carcinogen exposure with smoking of progressively reduced nicotine content cigarette. Cancer Epidemiol. Biomarkers Prev. 16, 2479-2485.

Benowitz, N. L. and Henningfield, J. E. (1994) Establishing a nicotine threshold for addiction-the implications for tobacco regulation. New Engl. J. Med. 331, 123-125.

Chaplin, J. F., and Burk, L. G. (1983) Agronomic, chemical, and smoke characteristics of flue-cured tobacco lines with different levels of total alkaloids. Crop Sci. 75, 133-136.

Chaplin, J. F., and Weeks, W. W. (1976) Association between percent total alkaloids and other traits in flue-cured tobacco. Crop Sci. 16, 416-418.

Curtin, S. J., Voytas, D. F. and Stupar, R. M. (2012) Genome engineering of crops with designer nucleases. Plant Genome 5, 42-50.

Dewey, R. E. and Lewis, R. S. (2014) Molecular biology-based approaches for facilitating compliance of future tobacco products in an FDA regulatory environment. Recent Adv. Tob. Sci. 40, 47-62.

Dewey, R. E. and Xie, J. (2013) Molecular genetics of alkaloid biosynthesis in *Nicotiana tabacum*. Phytochem. 94, 10-27.

Donny, E. C., Hatsukami, D. K., Benowitz, N. L., Sved, A. F., Tidey, J. W., and Cassidy, R. N. (2014) Reduced nicotine product standards for combustible tobacco: building an empirical basis for effective regulation. Prev. Medicine (in press, dx.doi.org/10.1016/j.ypmed.2014.06.020).

Gao, H., Smith, J., Yang, M., Jones, S., Djukanovic, V., Nicholson, M. G., West, A., Bidney, D., Falco, S. C., Jantz, D. and Lyznik, L. A. (2010) Heritable targeted mutagenesis in maize using a designed endonuclease. Plant J. 61, 176-187.

Hatsukami, D. K., Kotlyar, M., Hertsgaard, L. A., Zhang, Y., Carmella, S. G., Jensen, J. A., Allen, S. S., Shields, P. G., Murphy, S. E., Stepanov, I., and Hecht, S. S. (2010a) Reduced nicotine content cigarettes: effects on toxicant exposure, dependence and cessation. Addiction, 105, 343-355.

Hecht, S. S. (1998) Biochemistry, biology, and carcinogenicity of tobacco-specific N-nitrosamines. Chem. Res. Toxicol. 11, 559-603.

Hecht, S. S. (2003) Tobacco carcinogens, their biomarkers and tobacco induced cancers. Nat. Rev. Cancer 3, 733-744.

Hecht, S. S., and Hoffmann, D. (1989) The relevance of tobacco-specific nitrosamines to human cancer. Cancer Surveys. 8, 273-294.

Horsch, R. B., Fry, J. E., Hoffmann, N. L., Eichholtz, D., Rogers, S. G., Fraley, R. T., (1985) A simple and general-method for transferring genes into plants. Science 227, 1229-1231.

Kajikawa, M., Shoji, T., Kato, A. and Hashimoto, T. (2011) Vacuole-localized berberine bridge enzyme-like proteins are required for a late step of nicotine biosynthesis in tobacco. Plant Physiol. 155, 2010-2022.

Kidd, S., Melillo, A. and Jelesko, J. (2006) The A and B loci in tobacco regulate a network of stress response genes, few of which are associated with nicotine biosynthesis. Plant Mol. Biol. 60, 699-716.

Legg, P. D., Chaplin, J. F., and Collins, G. B. (1969) Inheritance of percent total alkaloids in *Nicotiana tabacum* L.: populations derived from crosses of low alkaloid lines with burley and flue-cured varieties. J. Hered. 60, 213-217.

Legg, P. D., and Collins, G. B. (1971) Inheritance of percent total alkaloids in *Nicotiana tabacum* L. II. Genetic effects of two loci in Burley 21 x LA Burley 21 populations. Can. J. Genet. Cytol. 13, 287-291.

Legg, P. D., Collins, G. B., and Littion, C. C. (1970) Registration of LA Burley 21 tobacco germplasm. Crop Sci. 10, 212.

Lewis, R. S., Bowen, S. W., Keogh, M. R. and Dewey, R. E. (2010) Three nicotine demethylase genes mediate nornicotine biosynthesis in *Nicotiana tabacum* L.: functional characterization of the CYP82E10 gene. Phytochem. 71, 1988-1998.

Lewis, R. S., Lopez, H. O., Bowen, S. W., Andres, K. R., Steede, W. T. and Dewey, R. E. (2015) Transgenic and mutation-based suppression of a Berberine Bridge Enzyme-Like (BBL) gene family reduces alkaloid content in field-grown plants. PLOS ONE 10, e0117273.

Lopez, H. O. (2011) Developing non-GMO tobacco cultivars with lower alkaloid content using a reverse genetics strategy. MS Thesis. North Carolina State University.

Puchta, H. and Fauser, F. (2014) Synthetic nucleases for genome engineering in plants: prospects for a bright future. Plant J. 78, 727-741.

Sierro, N., Battey, J. N. D., Ouadi, S., Bakaher, N., Bovet, L., Willig, A., Goepfert, S., Peitsch, M. C. and Ivanov, N. V. (2014) The tobacco genome sequence and its comparison with those of tomato and potato. Nat. Commun. 5, 3833.

Xie, J. H., Song, W., Maksymowicz, W., Jin, W., Cheah, K., Chen, W. X., Carnes, C., Ke, J., and Conkling, M. A. (2004) Biotechnology: a tool for reduced risk tobacco products—the nicotine experience from test tube to cigarette pack. Rev. Adv. Tob. Sci. 30, 17-37.

That which is claimed is:

1. A *Nicotiana* plant, wherein the plant:
(a) is modified so as to reduce the activity of at least one of BBLa, BBLb, and BBLc or to reduce expression of a nucleic acid encoding at least one of BBLa, BBLb, and BBLc; and
(b) comprises a mutation in at least one endogenous polynucleotide or combination of polynucleotides selected from the group consisting of:
(i) a polynucleotide having about 97% to about 100% sequence identity to SEQ ID NO:1 and a polynucleotide having about 97% to about 100% sequence identity to SEQ ID NO: 2;
(ii) a polynucleotide having about 97% to about 100% sequence identity to SEQ ID NO: 1 and a polynucleotide having about 97% to about 100% sequence identity to SEQ ID NO: 3;
(iii) a polynucleotide having about 97% to about 100% sequence identity to SEQ ID NO:2; and
(iv) a polynucleotide having about 97% to about 100% sequence identity to SEQ ID NO:3,
such that the *Nicotiana* plant has a nicotinic alkaloid content that is reduced as compared to a plant that is not modified per (a) and does not comprise the mutations of (b).

2. The *Nicotiana* plant of claim 1, wherein the plant is modified so as to reduce the activity of at least two of BBLa, BBLb, and BBLc or to reduce expression of a nucleic acid encoding at least two of BBLa, BBLb, and BBLc.

3. The *Nicotiana* plant of claim 2, wherein the *Nicotiana* plant is modified so as to reduce the activity of each of BBLa, BBLb, and BBLc or to reduce expression of a nucleic acid encoding each of BBLa, BBLb, and BBLc.

4. The *Nicotiana* plant of claim 3, wherein the plant comprises a mutation in each of at least two of the polynucleotides or the polynucleotide combinations of (i) (iv).

5. The *Nicotiana* plant of claim 4, wherein the plant comprises a mutation in each of the polynucleotides or the polynucleotide combinations of (i) (iv).

6. The *Nicotiana* plant of claim 3, wherein the plant has a nicotinic alkaloid content that is reduced by at least 90% as compared to a plant that is not modified per (a) and does not comprise the mutations of (b).

7. The *Nicotiana* plant of claim 6, wherein the plant has a nicotinic alkaloid content that is reduced by at least 95% as compared to a plant that is not modified per (a) and does not comprise the mutations of (b).

8. The *Nicotiana* plant of claim 6, wherein the plant has a nicotinic alkaloid content that is reduced by at least 97% as compared to a plant that is not modified per (a) and does not comprise the mutations of (b).

9. The *Nicotiana* plant of claim 1, wherein the plant:
(a) is modified so as to reduce the activity of each of BBLa, BBLb, and BBLc or to reduce expression of a nucleic acid encoding each of BBLa, BBLb, and BBLc, and
(b) comprises a mutation in at least polynucleotide (iv), and
wherein the nicotinic alkaloid content of the *Nicotiana* plant is reduced by at least 90% as compared to a plant that is not modified per (a) and does not comprise the mutations of (b).

10. A seed of the *Nicotiana* plant of claim 1, wherein the seed comprises a mutation in at least one of the polynucleotides or the polynucleotide combinations of (i)-(iv).

11. A progeny *Nicotiana* plant produced from the plant of claim 1, wherein the plant comprises the mutations in the at least one endogenous polynucleotide or combinations of polynucleotides [:
(a) is modified so as to reduce the activity of at least one of BBLa, BBLb, and BBLc or to reduce expression of a nucleic acid encoding at least one of BBLa, BBLb, and BBLc; and
(b) comprises a mutation in at least one endogenous polynucleotide or combination of polynucleotides selected from the group consisting of:
(i) a polynucleotide having about 97% to about 100% sequence identity to SEQ ID NO:1 and a polynucleotide having about 97% to about 100% sequence identity to SEQ ID NO: 2,
(ii) a polynucleotide having about 97% to about 100% sequence identity to SEQ ID NO: 1 and a polynucleotide having about 97% to about 100% sequence identity to SEQ ID NO: 3;
(iii) a polynucleotide having about 97% to about 100% sequence identity to SEQ ID NO:2; and (iv) a polynucleotide having about 97% to about 100% sequence identity to SEQ ID NO:3].

12. A crop comprising a plurality of *Nicotiana* plants of claim 1 planted together in an agricultural field, wherein the plants comprise the mutations in the at least one endogenous polynucleotide or combinations of polynucleotides [:
(a) are modified so as to reduce the activity of at least one of BBLa, BBLb, and BBLc or to reduce expression of a nucleic acid encoding at least one of BBLa, BBLb, and BBLc;
(b) comprise a mutation in at least one endogenous polynucleotide or combination of polynucleotides selected from the group consisting of:
(i) a polynucleotide having about 97% to about 100% sequence identity to SEQ ID NO:1 and a polynucleotide having about 97% to about 100% sequence identity to SEQ ID NO: 2;
(ii) a polynucleotide having about 97% to about 100% sequence identity to SEQ ID NO: 1 and a polynucleotide having about 97% to about 100% sequence identity to SEQ ID NO: 3;
(iii) a polynucleotide having about 97% to about 100% sequence identity to SEQ ID NO:2; and (iv) a polynucleotide having about 97% to about 100% sequence identity to SEQ ID NO:3].

* * * * *

SEQUENCE LISTING

<160> NUMBER OF SEQ ID NOS: 37

<210> SEQ ID NO 1
<211> LENGTH: 1704
<212> TYPE: DNA
<213> ORGANISM: Nicotiana tabacum

<400> SEQUENCE: 1

| | | |
|---|---|---|
| atgaaacgaa atatatccat gtttcttcag cttctgctca ttattctgat gatgatcagc | 60 |
| ttcttattta cttctcttct tgtaccttcg gtctctgcaa caactctcaa taccatttcc | 120 |
| acctgtttaa tcaattacaa agtcagtaac ttctctgttt acccaacaag gaatcatgct | 180 |
| ggtaatagtt actataactt gcttgatttc tccattcaga atctccgatt cgcagcgtgc | 240 |
| tctaaaccaa aaccaactgt cattatcgta ccagagagca aggagcagct ggtgagcagc | 300 |
| gttctgtgtt gcagacaagg ctcgtatgaa atcagagtaa ggtgcggtgg acacagttat | 360 |
| gaagggactt catcagtttc ctttgatggt tccccatttg tggtcattga tttgatgaaa | 420 |
| ttagacggcg tttcagtgga tgtggattca gaaaccgcgt gggtacaggg cggcgctaca | 480 |
| cttggccaga cttattatgc catttcccga gccagcaacg ttcatggatt ttcagctggt | 540 |
| tcttgcccaa cagttggggt tggcgggcac atttccgggg gtggttacgg attttttatcc | 600 |
| agaaaatatg gacttgctgc tgataacgtg gtggatgctc ttcttgttga tgcggaagga | 660 |
| cggctattag accgcaaagc catgggagaa gaaatctttt gggccatcag aggtggaggt | 720 |
| ggaggaattt ggggaatcat ttacgcctgg aaaatccgat tgctcaaagt gcccaagacc | 780 |
| gtgaccagtt tcataatccc taggcctggc tccaaacgat atgtgtccca actagttcac | 840 |
| aaatggcaac ttgttgcacc aaagttagag gatgaatttt atctatcgat ctccatgagc | 900 |
| tctcctagta aggaaacat tcctattgaa ataaatgccc aattcagcgg atttttaccta | 960 |
| ggtacaaaaa ccgaagccat ttccatcttg aatgaggcct tttcggagtt gggagttctg | 1020 |
| gaaggtgact gcaaagaaat gagttggatt gaatcaacac ttttcttctc cgaattaaat | 1080 |
| gacgttgcga attcctccga tgtctctcgt ttgaaagagc gttactttga aaacaaatca | 1140 |
| tacttcaaag ccaaatcaga ctatgtgaag accccaattt cagtgggtgg gattatgacg | 1200 |
| gctcttaatg ttcttgagaa agaacccaac ggacatgtca tcttggaccc ttatggtgga | 1260 |
| gccatgcaaa gaattagtga ggaagctatt gctttccctc atagaaaggg taaccttttc | 1320 |
| ggaattcaat atctagtagt gtggaaagaa aaggacaata ataatattgt caagagcaat | 1380 |
| attgggtaca tagagtggat aagagagttt acaatacaa tggcaccca tgtttcaagt | 1440 |
| tcacctaggg cagcttatgt caactacatg gatctggacc ttggagtgat ggacgactac | 1500 |
| ttattgccat gtactagtac tactgcgtct gctaatcatg ccgtggagag agcaagggtc | 1560 |
| tggggtgaaa agtatttctt gaataactat gatagattgg tcaaagctaa gacaaaaatt | 1620 |
| gacccactaa acgttttcg acatcaacag ggcatccctc ctttgttcgc ctcaatgcaa | 1680 |
| gagtataacct atagtagtaa atga | 1704 |

<210> SEQ ID NO 2
<211> LENGTH: 1701
<212> TYPE: DNA
<213> ORGANISM: Nicotiana tabacum

<400> SEQUENCE: 2

| | | |
|---|---|---|
| atgaaacgaa atatatccat gtctcttcag cgtttgctca taattctgat gatgatcagc | 60 |
| ttcttattta cttctcttct tgtaccttcc gtctctgcta caaatctcaa taccatttcc | 120 |

```
acctgtttga tcaattacaa agtcagtaac ttctctgttt atccaacaag gaatcatgct    180
ggtaataggt actataactt gcttgatttc tccattcaga atctccgatt cgcagcgtcc    240
tctaaaccaa aaccaacggt cattatcgta ccagagagca aggagcagct ggtgagcagc    300
gttctgtgtt gcagacaagg ttcttatgaa atcagataa ggtgcggagg acacagttat     360
gaagggactt cttacgtttc ctttgatggt tccccatttg tggtcattga tttgatgaaa    420
ttagatgatg tttcggtaga tttggattcc gaaaccgcgt gggtacaagg tggcgctaca    480
cttggccaga cttattatgc catttcccgg gccagtgacg ttcatggatt ttcagctggt    540
tcttgcccaa cagttggggt tgggggccac atttccgggg gtggctttgg atttttatca    600
agaaaatatg gacttgctgc tgataacgtg gtggatgctc ttcttgttga tgcggaagga    660
cggctattag accgcaaagc catgggagaa gaagtgtttt gggccatcag aggtggtggt    720
ggaggaattt ggggaatcat ttacgcctgg aaaatccgat tgctcaaagt gcccaagact    780
gtgactagtt tcatagtccc taggcctggc tccaaacgat atgtgtccca actagttcac    840
aaatggcaac ttgttgcacc aaagttagac gatgactttt atctatcgat ctccatgagc    900
tctgctagta aaggaaacat tcctattgaa ataaatgccc aattcagcgg atttacccta    960
ggtacaaaaa ccgaagccat ttccatcttg aatgaggcct ttccggagtt gggagttgtg   1020
gaaagtgact gcaaagaaat gagttggatt gaatcaacac ttttcttctc cgaattagat   1080
aacgttgcga cacctccga tgtctctcgt ttgaaagagc gttactttga aaacaaatca    1140
tacttcaaag ccaaatcaga ccatgtgaag accccaattt cagtgggagg gattatgaca   1200
gctcttgatg ttcttgagaa agaaccaaat ggacatgtca tctttgaccc ttatggtgca   1260
gccatgcaga gaattagcga ggaagctatt gctttccctc atagaaaggg taacctattc   1320
agaattcaat atctagtagt gtggaaagaa aaggacaata ataatattgc caagagcaat   1380
gggtacatag agtggataag agagttttac aatacaatgg caccccatgt ttctagttca   1440
cctagggcag cttatgtcaa ctatatggat ctggaccttg gagtgatgga cgactactta   1500 atgctaaaata ctagtattac tgcctctgct gatcatgccg tggagagagc aagggtctgg   1560
ggtgaaaagt atttcttgaa taactatgat agattggtca aagctaagac aaaaattgac   1620
ccactaaacg ttttttcgaca tcaacagggc atccctccta tgttcgcctc aatgccagag   1680 cataccata gtagtaaatg a                                               1701

<210> SEQ ID NO 3
<211> LENGTH: 1698
<212> TYPE: DNA
<213> ORGANISM: Nicotiana tabacum

<400> SEQUENCE: 3
atgtttccaa tcataattct gatcagcttt tcatttactt tcctctttgc tagtgttact     60
agtggagcag gaggagttac aaatctttcc acctgtttaa tcaaccacaa tgtccataac    120
ttctctattt accccacaaa gaatgatcaa agtagtagta attactttaa cttgctcgat    180
ttttcccttc agaatcttcg atttgctgca tcttacatgc cgaaaccaac ggtcattatc    240
ctaccaaaca gcaaagagga gctcgtgagt accattcttt gttgcagaca acatctttat    300
gaaatcagag taaggtgcgg aggacacagt tacgagggaa cttcttacgt tcctttgac     360 ggttcccctt tcgtgatcgt tgacttgatg aaattgaacg acgttcagt agatttggat     420 tccgaaacag cttgggctca gggcggcgca acaattggcc aaatttatta cgccattcc     480
```

-continued

```
agggttagtg acgttcatgc attttcagca ggttcgggac caacagtagg atctggaggt    540
catatttcag gtggcggctt tggactaatg tccagaaaat tcggactcgc tgctgatagt    600
gtcgttgatg ctcttctaat tgatgctgaa ggacggttat tagaccggaa agccatggga    660
gaagacgtat tttgggcaat cagaggtggc ggcggtggaa attgggggaat tatttatgcc   720
tggaaaattc gattactcaa agtgcctaaa atcgtaacaa cttgtatgat ctataggcct    780
ggatccaaac aatacgtggc tcaactactt cagaaatggc aaatagttac tccaaatttg    840
gccgatgatt ttactctagg agtactcatg agacctatag atctgcgggc ggatatgaat    900
tacggaaata ctactcctat tgaaacattt ccccaattca atgcacttta tttgggtcca    960
aaaactgaag cggtttccat attaaatgag gcatttccag agctggacgc taagaatgat   1020
gacgccaaag aaatgacttg gattgagtca gcacttttct tttccgaatt agataacgta   1080
ttcgggaact cctctgacga tatctcccgt ttgaaagaac gctacatgga cgcaaaaact   1140
ttcttcaaag gcaaatcaga ttttgtgaag actccatttt caatggacgc gatgatgaca   1200
gctcttgttg aactcgagaa aaaccccaag tcattccttg tcttcgatcc ttatggcgga   1260
gtcatggaca agattagtga tcaagctatt gctttccctc atcgaaaggg taaccttttc   1320
gcggttcaat attatgcatt ttggaacgaa gaggacgatg ccaagagcaa cgagtacata   1380
gagtggacaa ggggatttta caataaaatg gcgccttttg tttcaagctc gccaagggga   1440
gcttatatca actacttgga tatggatctt ggagtgaata tggacgacga ctacttactg   1500
cgaaatgcta gtagtcgtag ttcttcttcc tctgttgatg ctgtggagag agctagagcg   1560
tggggtgaaa tgtatttctt gcataactat gataggttgg ttaaagctaa gacacaaatt   1620
gatccactaa atgtttttcg acatgaacag agtataccte ctatgcttgg ttcaacgcaa   1680
gagcacagta gtgaatga                                                  1698
```

<210> SEQ ID NO 4
<211> LENGTH: 567
<212> TYPE: PRT
<213> ORGANISM: Nicotiana tabacum

<400> SEQUENCE: 4

```
Met Lys Arg Asn Ile Ser Met Phe Leu Gln Leu Leu Leu Ile Ile Leu
1               5                   10                  15

Met Met Ile Ser Phe Leu Phe Thr Ser Leu Leu Val Pro Ser Val Ser
            20                  25                  30

Ala Thr Thr Leu Asn Thr Ile Ser Thr Cys Leu Ile Asn Tyr Lys Val
        35                  40                  45

Ser Asn Phe Ser Val Tyr Pro Thr Arg Asn His Ala Gly Asn Ser Tyr
    50                  55                  60

Tyr Asn Leu Leu Asp Phe Ser Ile Gln Asn Leu Arg Phe Ala Ala Cys
65                  70                  75                  80

Ser Lys Pro Lys Pro Thr Val Ile Ile Val Pro Glu Ser Lys Glu Gln
                85                  90                  95

Leu Val Ser Ser Val Leu Cys Cys Arg Gln Gly Ser Tyr Glu Ile Arg
            100                 105                 110

Val Arg Cys Gly Gly His Ser Tyr Glu Gly Thr Ser Ser Val Ser Phe
        115                 120                 125

Asp Gly Ser Pro Phe Val Val Ile Asp Leu Met Lys Leu Asp Gly Val
    130                 135                 140

Ser Val Asp Val Asp Ser Glu Thr Ala Trp Val Gln Gly Gly Ala Thr
145                 150                 155                 160
```

```
Leu Gly Gln Thr Tyr Tyr Ala Ile Ser Arg Ala Ser Asn Val His Gly
                165                 170                 175

Phe Ser Ala Gly Ser Cys Pro Thr Val Gly Val Gly His Ile Ser
            180                 185                 190

Gly Gly Gly Tyr Gly Phe Leu Ser Arg Lys Tyr Gly Leu Ala Ala Asp
            195                 200                 205

Asn Val Val Asp Ala Leu Leu Val Asp Ala Glu Gly Arg Leu Leu Asp
        210                 215                 220

Arg Lys Ala Met Gly Glu Glu Ile Phe Trp Ala Ile Arg Gly Gly Gly
225                 230                 235                 240

Gly Gly Ile Trp Gly Ile Ile Tyr Ala Trp Lys Ile Arg Leu Leu Lys
            245                 250                 255

Val Pro Lys Thr Val Thr Ser Phe Ile Ile Pro Arg Pro Gly Ser Lys
            260                 265                 270

Arg Tyr Val Ser Gln Leu Val His Lys Trp Gln Leu Val Ala Pro Lys
        275                 280                 285

Leu Glu Asp Glu Phe Tyr Leu Ser Ile Ser Met Ser Ser Pro Ser Lys
        290                 295                 300

Gly Asn Ile Pro Ile Glu Ile Asn Ala Gln Phe Ser Gly Phe Tyr Leu
305                 310                 315                 320

Gly Thr Lys Thr Glu Ala Ile Ser Ile Leu Asn Glu Ala Phe Ser Glu
                325                 330                 335

Leu Gly Val Leu Glu Gly Asp Cys Lys Glu Met Ser Trp Ile Glu Ser
            340                 345                 350

Thr Leu Phe Phe Ser Glu Leu Asp Asp Val Ala Asn Ser Ser Asp Val
            355                 360                 365

Ser Arg Leu Lys Glu Arg Tyr Phe Glu Asn Lys Ser Tyr Phe Lys Ala
        370                 375                 380

Lys Ser Asp Tyr Val Lys Thr Pro Ile Ser Val Gly Gly Ile Met Thr
385                 390                 395                 400

Ala Leu Asn Val Leu Glu Lys Glu Pro Asn Gly His Val Ile Leu Asp
                405                 410                 415

Pro Tyr Gly Gly Ala Met Gln Arg Ile Ser Glu Ala Ile Ala Phe
            420                 425                 430

Pro His Arg Lys Gly Asn Leu Phe Gly Ile Gln Tyr Leu Val Val Trp
            435                 440                 445

Lys Glu Lys Asp Asn Asn Asn Ile Val Lys Ser Asn Ile Gly Tyr Ile
        450                 455                 460

Glu Trp Ile Arg Glu Phe Tyr Asn Thr Met Ala Pro His Val Ser Ser
465                 470                 475                 480

Ser Pro Arg Ala Ala Tyr Val Asn Tyr Met Asp Leu Asp Leu Gly Val
            485                 490                 495

Met Asp Asp Tyr Leu Leu Pro Cys Thr Ser Thr Thr Ala Ser Ala Asn
            500                 505                 510

His Ala Val Glu Arg Ala Arg Val Trp Gly Glu Lys Tyr Phe Leu Asn
        515                 520                 525

Asn Tyr Asp Arg Leu Val Lys Ala Lys Thr Lys Ile Asp Pro Leu Asn
        530                 535                 540

Val Phe Arg His Gln Gln Gly Ile Pro Pro Leu Phe Ala Ser Met Gln
545                 550                 555                 560

Glu Tyr Thr Tyr Ser Ser Lys
                565
```

<210> SEQ ID NO 5
<211> LENGTH: 566
<212> TYPE: PRT
<213> ORGANISM: Nicotiana tabacum

<400> SEQUENCE: 5

Met Lys Arg Asn Ile Ser Met Ser Leu Gln Arg Leu Leu Ile Ile Leu
1               5                   10                  15

Met Met Ile Ser Phe Leu Phe Thr Ser Leu Leu Val Pro Ser Val Ser
            20                  25                  30

Ala Thr Asn Leu Asn Thr Ile Ser Thr Cys Leu Ile Asn Tyr Lys Val
        35                  40                  45

Ser Asn Phe Ser Val Tyr Pro Thr Arg Asn His Ala Gly Asn Arg Tyr
    50                  55                  60

Tyr Asn Leu Leu Asp Phe Ser Ile Gln Asn Leu Arg Phe Ala Ala Ser
65                  70                  75                  80

Ser Lys Pro Lys Pro Thr Val Ile Ile Val Pro Glu Ser Lys Glu Gln
                85                  90                  95

Leu Val Ser Ser Val Leu Cys Cys Arg Gln Gly Ser Tyr Glu Ile Arg
            100                 105                 110

Val Arg Cys Gly Gly His Ser Tyr Glu Gly Thr Ser Tyr Val Ser Phe
        115                 120                 125

Asp Gly Ser Pro Phe Val Val Ile Asp Leu Met Lys Leu Asp Asp Val
    130                 135                 140

Ser Val Asp Leu Asp Ser Glu Thr Ala Trp Val Gln Gly Gly Ala Thr
145                 150                 155                 160

Leu Gly Gln Thr Tyr Tyr Ala Ile Ser Arg Ala Ser Asp Val His Gly
                165                 170                 175

Phe Ser Ala Gly Ser Cys Pro Thr Val Gly Val Gly Gly His Ile Ser
            180                 185                 190

Gly Gly Gly Phe Gly Phe Leu Ser Arg Lys Tyr Gly Leu Ala Ala Asp
        195                 200                 205

Asn Val Val Asp Ala Leu Leu Val Asp Ala Glu Gly Arg Leu Leu Asp
    210                 215                 220

Arg Lys Ala Met Gly Glu Glu Val Phe Trp Ala Ile Arg Gly Gly Gly
225                 230                 235                 240

Gly Gly Ile Trp Gly Ile Ile Tyr Ala Trp Lys Ile Arg Leu Leu Lys
                245                 250                 255

Val Pro Lys Thr Val Thr Ser Phe Ile Val Pro Arg Pro Gly Ser Lys
            260                 265                 270

Arg Tyr Val Ser Gln Leu Val His Lys Trp Gln Leu Val Ala Pro Lys
        275                 280                 285

Leu Asp Asp Asp Phe Tyr Leu Ser Ile Ser Met Ser Ser Ala Ser Lys
    290                 295                 300

Gly Asn Ile Pro Ile Glu Ile Asn Ala Gln Phe Ser Gly Phe Tyr Leu
305                 310                 315                 320

Gly Thr Lys Thr Glu Ala Ile Ser Ile Leu Asn Glu Ala Phe Pro Glu
                325                 330                 335

Leu Gly Val Val Glu Ser Asp Cys Lys Glu Met Ser Trp Ile Glu Ser
            340                 345                 350

Thr Leu Phe Phe Ser Glu Leu Asp Asn Val Ala Asn Thr Ser Asp Val
        355                 360                 365

Ser Arg Leu Lys Glu Arg Tyr Phe Glu Asn Lys Ser Tyr Phe Lys Ala
    370                 375                 380

Lys Ser Asp His Val Lys Thr Pro Ile Ser Val Gly Gly Ile Met Thr
385                 390                 395                 400

Ala Leu Asp Val Leu Glu Lys Glu Pro Asn Gly His Val Ile Phe Asp
            405                 410                 415

Pro Tyr Gly Ala Ala Met Gln Arg Ile Ser Glu Glu Ala Ile Ala Phe
        420                 425                 430

Pro His Arg Lys Gly Asn Leu Phe Arg Ile Gln Tyr Leu Val Val Trp
    435                 440                 445

Lys Glu Lys Asp Asn Asn Ile Ala Lys Ser Asn Gly Tyr Ile Glu
450                 455                 460

Trp Ile Arg Glu Phe Tyr Asn Thr Met Ala Pro His Val Ser Ser
465                 470                 475                 480

Pro Arg Ala Ala Tyr Val Asn Tyr Met Asp Leu Asp Leu Gly Val Met
            485                 490                 495

Asp Asp Tyr Leu Met Leu Asn Thr Ser Ile Thr Ala Ser Ala Asp His
        500                 505                 510

Ala Val Glu Arg Ala Arg Val Trp Gly Glu Lys Tyr Phe Leu Asn Asn
    515                 520                 525

Tyr Asp Arg Leu Val Lys Ala Lys Thr Lys Ile Asp Pro Leu Asn Val
530                 535                 540

Phe Arg His Gln Gln Gly Ile Pro Pro Met Phe Ala Ser Met Pro Glu
545                 550                 555                 560

His Thr Tyr Ser Ser Lys
            565

<210> SEQ ID NO 6
<211> LENGTH: 565
<212> TYPE: PRT
<213> ORGANISM: Nicotiana tabacum

<400> SEQUENCE: 6

Met Phe Pro Ile Ile Leu Ile Ser Phe Ser Phe Thr Phe Leu Phe
1               5                   10                  15

Ala Ser Val Thr Ser Gly Ala Gly Gly Val Thr Asn Leu Ser Thr Cys
            20                  25                  30

Leu Ile Asn His Asn Val His Asn Phe Ser Ile Tyr Pro Thr Lys Asn
        35                  40                  45

Asp Gln Ser Ser Ser Asn Tyr Phe Asn Leu Leu Asp Phe Ser Leu Gln
    50                  55                  60

Asn Leu Arg Phe Ala Ala Ser Tyr Met Pro Lys Pro Thr Val Ile Ile
65                  70                  75                  80

Leu Pro Asn Ser Lys Glu Glu Leu Val Ser Thr Ile Leu Cys Cys Arg
                85                  90                  95

Gln Thr Ser Tyr Glu Ile Arg Val Arg Cys Gly Gly His Ser Tyr Glu
            100                 105                 110

Gly Thr Ser Tyr Val Ser Phe Asp Gly Ser Pro Phe Val Ile Val Asp
        115                 120                 125

Leu Met Lys Leu Asp Asp Val Ser Val Asp Leu Asp Ser Glu Thr Ala
    130                 135                 140

Trp Ala Gln Gly Gly Ala Thr Ile Gly Gln Ile Tyr Tyr Ala Ile Ser
145                 150                 155                 160

Arg Val Ser Asp Val His Ala Phe Ser Ala Gly Ser Gly Pro Thr Val
                165                 170                 175

Gly Ser Gly Gly His Ile Ser Gly Gly Gly Phe Gly Leu Met Ser Arg

```
            180                 185                 190
Lys Phe Gly Leu Ala Ala Asp Ser Val Val Asp Ala Leu Leu Ile Asp
        195                 200                 205

Ala Glu Gly Arg Leu Leu Asp Arg Lys Ala Met Gly Glu Asp Val Phe
    210                 215                 220

Trp Ala Ile Arg Gly Gly Gly Asn Trp Gly Ile Ile Tyr Ala
225                 230                 235                 240

Trp Lys Ile Arg Leu Leu Lys Val Pro Lys Ile Val Thr Thr Cys Met
                245                 250                 255

Ile Tyr Arg Pro Gly Ser Lys Gln Tyr Val Ala Gln Leu Leu Gln Lys
            260                 265                 270

Trp Gln Ile Val Thr Pro Asn Leu Ala Asp Asp Phe Thr Leu Gly Val
        275                 280                 285

Leu Met Arg Pro Ile Asp Leu Arg Ala Asp Met Asn Tyr Gly Asn Thr
    290                 295                 300

Thr Pro Ile Glu Thr Phe Pro Gln Phe Asn Ala Leu Tyr Leu Gly Pro
305                 310                 315                 320

Lys Thr Glu Ala Val Ser Ile Leu Asn Glu Ala Phe Pro Glu Leu Asp
                325                 330                 335

Ala Lys Asn Asp Asp Ala Lys Glu Met Thr Trp Ile Glu Ser Ala Leu
            340                 345                 350

Phe Phe Ser Glu Leu Asp Asn Val Phe Gly Asn Ser Ser Asp Asp Ile
        355                 360                 365

Ser Arg Leu Lys Glu Arg Tyr Met Asp Ala Lys Thr Phe Phe Lys Gly
    370                 375                 380

Lys Ser Asp Phe Val Lys Thr Pro Phe Ser Met Asp Ala Met Met Thr
385                 390                 395                 400

Ala Leu Val Glu Leu Glu Lys Asn Pro Lys Ser Phe Leu Val Phe Asp
                405                 410                 415

Pro Tyr Gly Gly Val Met Asp Lys Ile Ser Asp Gln Ala Ile Ala Phe
            420                 425                 430

Pro His Arg Lys Gly Asn Leu Phe Ala Val Gln Tyr Tyr Ala Phe Trp
        435                 440                 445

Asn Glu Glu Asp Asp Ala Lys Ser Asn Glu Tyr Ile Glu Trp Thr Arg
    450                 455                 460

Gly Phe Tyr Asn Lys Met Ala Pro Phe Val Ser Ser Pro Arg Gly
465                 470                 475                 480

Ala Tyr Ile Asn Tyr Leu Asp Met Asp Leu Gly Val Asn Met Asp Asp
                485                 490                 495

Asp Tyr Leu Leu Arg Asn Ala Ser Ser Arg Ser Ser Ser Ser Val
            500                 505                 510

Asp Ala Val Glu Arg Ala Arg Ala Trp Gly Glu Met Tyr Phe Leu His
        515                 520                 525

Asn Tyr Asp Arg Leu Val Lys Ala Lys Thr Gln Ile Asp Pro Leu Asn
    530                 535                 540

Val Phe Arg His Glu Gln Ser Ile Pro Pro Met Leu Gly Ser Thr Gln
545                 550                 555                 560

Glu His Ser Ser Glu
                565

<210> SEQ ID NO 7
<211> LENGTH: 22
<212> TYPE: DNA
<213> ORGANISM: Nicotiana tabacum
```

<400> SEQUENCE: 7
gaggagctcg tgagtaccat tc                                                  22

<210> SEQ ID NO 8
<211> LENGTH: 22
<212> TYPE: DNA
<213> ORGANISM: Nicotiana tabacum

<400> SEQUENCE: 8
gtcattatcg taccagagag ca                                                  22

<210> SEQ ID NO 9
<211> LENGTH: 83
<212> TYPE: DNA
<213> ORGANISM: Nicotiana tabacum

<400> SEQUENCE: 9
catcttacat gccgaaacca acggtcatta tcctaccaaa cagcaaagag gagctcgtga         60
gtaccattct tgttgcaga caa                                                  83

<210> SEQ ID NO 10
<211> LENGTH: 77
<212> TYPE: DNA
<213> ORGANISM: Artificial
<220> FEATURE:
<223> OTHER INFORMATION: Mutated BBL nucletotide sequence

<400> SEQUENCE: 10
catcttacat gccgaaacca acggtcatta tcctaccaaa cagcaaagag gagggtacca         60
ttctttgttg cagacaa                                                        77

<210> SEQ ID NO 11
<211> LENGTH: 81
<212> TYPE: DNA
<213> ORGANISM: Artificial
<220> FEATURE:
<223> OTHER INFORMATION: Mutated BBL nucletotide sequence

<400> SEQUENCE: 11
catcttacat gccgaaacca acggtcatta tcctaccaaa cagcaaagag gagctcgagt         60
accattcttt gttgcagaca a                                                   81

<210> SEQ ID NO 12
<211> LENGTH: 74
<212> TYPE: DNA
<213> ORGANISM: Artificial
<220> FEATURE:
<223> OTHER INFORMATION: Mutated BBL nucletotide sequence

<400> SEQUENCE: 12
catcttacat gccgaaacca acggtcatta tcctaccaaa cagcaaagag agtaccattc         60
tttgttgcag acaa                                                           74

<210> SEQ ID NO 13
<211> LENGTH: 57
<212> TYPE: DNA
<213> ORGANISM: Artificial
<220> FEATURE:
<223> OTHER INFORMATION: Mutated BBL nucletotide sequence

<400> SEQUENCE: 13
catctattaa ccccacaaag aatgatcaaa gtaagtacca ttctttgttg cagacaa    57

<210> SEQ ID NO 14
<211> LENGTH: 75
<212> TYPE: DNA
<213> ORGANISM: Artificial
<220> FEATURE:
<223> OTHER INFORMATION: Mutated BBL nucletotide sequence

<400> SEQUENCE: 14
catcttacat gccgaaacca acggtcatta tcctaccaaa cagcaaagag gagcttctta    60
cacttgtgca gacaa    75

<210> SEQ ID NO 15
<211> LENGTH: 69
<212> TYPE: DNA
<213> ORGANISM: Artificial
<220> FEATURE:
<223> OTHER INFORMATION: Mutated BBL nucletotide sequence

<400> SEQUENCE: 15
catcttacat gccgaaacca acggtcatta tcctaccaaa cagcaaagag gattctttgt    60
tgcagacaa    69

<210> SEQ ID NO 16
<211> LENGTH: 82
<212> TYPE: DNA
<213> ORGANISM: Artificial
<220> FEATURE:
<223> OTHER INFORMATION: Mutated BBL nucletotide sequence

<400> SEQUENCE: 16
catcttacat gccgaaacca acggtcatta tcctaccaaa cagcaaagag gagctcggag    60
taccattctt tgttgcagac aa    82

<210> SEQ ID NO 17
<211> LENGTH: 51
<212> TYPE: DNA
<213> ORGANISM: Artificial
<220> FEATURE:
<223> OTHER INFORMATION: Mutated BBL nucletotide sequence

<400> SEQUENCE: 17
catcttacat gccgaaacca acggtcatta tccattcttt gttgcagaca a    51

<210> SEQ ID NO 18
<211> LENGTH: 72
<212> TYPE: DNA
<213> ORGANISM: Nicotiana tabacum

<400> SEQUENCE: 18
tctccgattc gcagcgtgct ctaaaccaaa accaactgtc attatcgtac cagagagcaa    60
ggagcagctg gt    72

<210> SEQ ID NO 19
<211> LENGTH: 35
<212> TYPE: DNA
<213> ORGANISM: Artificial
<220> FEATURE:
<223> OTHER INFORMATION: Mutated BBL nucletotide sequence

<400> SEQUENCE: 19
aactagtcta aaccagagag caaggagcag ctggt    35

<210> SEQ ID NO 20
<211> LENGTH: 57
<212> TYPE: DNA
<213> ORGANISM: Artificial
<220> FEATURE:
<223> OTHER INFORMATION: Mutated BBL nucletotide sequence

<400> SEQUENCE: 20
tctccgattc gcagcgtgct ctaaaccaaa actaccagag agcaaggagc agctggt      57

<210> SEQ ID NO 21
<211> LENGTH: 71
<212> TYPE: DNA
<213> ORGANISM: Artificial
<220> FEATURE:
<223> OTHER INFORMATION: Mutated BBL nucletotide sequence

<400> SEQUENCE: 21
tctccgattc gcagcgtgct ctaaaccaaa accaactgtc attatcgtac agagagcaag    60
gagcagctgg t                                                        71

<210> SEQ ID NO 22
<211> LENGTH: 54
<212> TYPE: DNA
<213> ORGANISM: Artificial
<220> FEATURE:
<223> OTHER INFORMATION: Mutated BBL nucletotide sequence

<400> SEQUENCE: 22
tctccgattc gcagcgtgct ctaaaccaaa accaactgtc aaggagcagg tggt          54

<210> SEQ ID NO 23
<211> LENGTH: 84
<212> TYPE: DNA
<213> ORGANISM: Artificial
<220> FEATURE:
<223> OTHER INFORMATION: Mutated BBL nucletotide sequence

<400> SEQUENCE: 23
tctccgattc gcagcgtgct ctaaaccaaa accaactgtc attatagtaa ctatcattaa    60
accagagagc aaggagcagc tggt                                          84

<210> SEQ ID NO 24
<211> LENGTH: 43
<212> TYPE: DNA
<213> ORGANISM: Artificial
<220> FEATURE:
<223> OTHER INFORMATION: Mutated BBL nucletotide sequence

<400> SEQUENCE: 24
tctccgattc gcagcgtata ccagagagca aggagcagct ggt                     43

<210> SEQ ID NO 25
<211> LENGTH: 53
<212> TYPE: DNA
<213> ORGANISM: Artificial
<220> FEATURE:
<223> OTHER INFORMATION: Mutated BBL nucletotide sequence

<400> SEQUENCE: 25
tctccgattc gcagcgtgct ctaaaccaaa accaactgtc attatcgtaa ggt           53

<210> SEQ ID NO 26

```
<211> LENGTH: 69
<212> TYPE: DNA
<213> ORGANISM: Artificial
<220> FEATURE:
<223> OTHER INFORMATION: Mutated BBL nucletotide sequence

<400> SEQUENCE: 26
tctccgattc gcagcgtgct ctaaaccaaa accaactgtc gcagtaccag agagcaagga      60
gcagctggt                                                             69

<210> SEQ ID NO 27
<211> LENGTH: 72
<212> TYPE: DNA
<213> ORGANISM: Nicotiana tabacum

<400> SEQUENCE: 27
tctccgattc gcagcgtcct ctaaaccaaa accaacggtc attatcgtac cagagagcaa      60
ggagcagctg gt                                                         72

<210> SEQ ID NO 28
<211> LENGTH: 67
<212> TYPE: DNA
<213> ORGANISM: Artificial
<220> FEATURE:
<223> OTHER INFORMATION: Mutated BBL nucletotide sequence

<400> SEQUENCE: 28
tctccgattc gcagcgtcct ctaaaccaaa accaacggtc attaccagag agcaaggagc      60
agctggt                                                               67

<210> SEQ ID NO 29
<211> LENGTH: 44
<212> TYPE: DNA
<213> ORGANISM: Artificial
<220> FEATURE:
<223> OTHER INFORMATION: Mutated BBL nucletotide sequence

<400> SEQUENCE: 29
tctccgattc gcagcgtcct ctaatgaaat cagagtaagc tggt                      44

<210> SEQ ID NO 30
<211> LENGTH: 84
<212> TYPE: DNA
<213> ORGANISM: Artificial
<220> FEATURE:
<223> OTHER INFORMATION: Mutated BBL nucletotide sequence

<400> SEQUENCE: 30
tctccgattc gcagcgtcct ctaaaccaaa accaacggtc attatcgtac acagttatga     60
agcgttctgg agagcaagga gcag                                            84

<210> SEQ ID NO 31
<211> LENGTH: 47
<212> TYPE: DNA
<213> ORGANISM: Artificial
<220> FEATURE:
<223> OTHER INFORMATION: Mutated BBL nucletotide sequence

<400> SEQUENCE: 31
tctccgattc gcagcgtcct ctaaaccaaa accaaggagc agctggt                   47

<210> SEQ ID NO 32
<211> LENGTH: 67
```

```
<212> TYPE: DNA
<213> ORGANISM: Artificial
<220> FEATURE:
<223> OTHER INFORMATION: Mutated BBL nucletotide sequence

<400> SEQUENCE: 32
tctccgattc gcagcgtcct ctaaaccaaa accaacggtc attatcagag agcaaggagc     60
agctggt                                                              67

<210> SEQ ID NO 33
<211> LENGTH: 57
<212> TYPE: DNA
<213> ORGANISM: Artificial
<220> FEATURE:
<223> OTHER INFORMATION: Mutated BBL nucletotide sequence

<400> SEQUENCE: 33
tctccgattc gcagcgtcct ctaaaccaaa accaacgtta aaaaggagc agctggt        57

<210> SEQ ID NO 34
<211> LENGTH: 47
<212> TYPE: DNA
<213> ORGANISM: Artificial
<220> FEATURE:
<223> OTHER INFORMATION: Mutated BBL nucletotide sequence

<400> SEQUENCE: 34
tctccgattc gcagcgtcct ctaaaccaaa accaacgaac agctggt                  47

<210> SEQ ID NO 35
<211> LENGTH: 33
<212> TYPE: DNA
<213> ORGANISM: Artificial
<220> FEATURE:
<223> OTHER INFORMATION: Mutated BBL nucletotide sequence

<400> SEQUENCE: 35
tctccgattc gcagagacca aggagccgct ggt                                 33

<210> SEQ ID NO 36
<211> LENGTH: 58
<212> TYPE: DNA
<213> ORGANISM: Artificial
<220> FEATURE:
<223> OTHER INFORMATION: Mutated BBL nucletotide sequence

<400> SEQUENCE: 36
tctccgattc gcagcgtcct ctaaaccaaa accaaccaga gagcaaggag cagctggt      58

<210> SEQ ID NO 37
<211> LENGTH: 56
<212> TYPE: DNA
<213> ORGANISM: Artificial
<220> FEATURE:
<223> OTHER INFORMATION: Mutated BBL nucletotide sequence

<400> SEQUENCE: 37
tctccgattc gcagcgtcct ctaaaccaaa accaacggtc attatcgtac gctggt        56
```